(12) United States Patent
Corsa et al.

(10) Patent No.: US 10,017,802 B2
(45) Date of Patent: Jul. 10, 2018

(54) **PROCESS FOR THE PRODUCTION OF HYALURONIC ACID IN *ESCHERICHIA COLI* OR *BACILLUS SUBTILIS***

(71) Applicant: FIDIA FARMACEUTICI S.P.A., Abano Terme (PD) (IT)

(72) Inventors: Vincenza Corsa, Abano Terme (IT); Alessandro Negro, Padua (IT); Susanna Vaccaro, Abano Terme (IT); Luciano Messina, Abano Terme (IT)

(73) Assignee: FIDIA FARMACEUTICI S.P.A., Abano Terme (PD) (IT)

( * ) Notice: Subject to any disclaimer, the term of this patent is extended or adjusted under 35 U.S.C. 154(b) by 0 days.

(21) Appl. No.: 15/045,704

(22) Filed: Feb. 17, 2016

(65) Prior Publication Data

US 2016/0237465 A1    Aug. 18, 2016

Related U.S. Application Data

(62) Division of application No. 13/821,947, filed as application No. PCT/EP2011/065642 on Sep. 9, 2011, now Pat. No. 9,290,785.

(30) Foreign Application Priority Data

Sep. 9, 2010 (IT) .............................. MI2010A1642

(51) Int. Cl.
| | | |
|---|---|---|
| *C12P 19/26* | (2006.01) | |
| *C08B 37/08* | (2006.01) | |
| *C12N 9/04* | (2006.01) | |
| *C12N 9/10* | (2006.01) | |
| *C12N 9/12* | (2006.01) | |
| *C12N 9/92* | (2006.01) | |
| *C12N 15/75* | (2006.01) | |
| *C12N 1/20* | (2006.01) | |
| *C12N 15/63* | (2006.01) | |

(52) U.S. Cl.
CPC .......... *C12P 19/26* (2013.01); *C08B 37/0072* (2013.01); *C12N 1/20* (2013.01); *C12N 9/0006* (2013.01); *C12N 9/1051* (2013.01); *C12N 9/1241* (2013.01); *C12N 9/92* (2013.01); *C12N 15/635* (2013.01); *C12N 15/75* (2013.01); *C12Y 101/01022* (2013.01); *C12Y 204/01212* (2013.01); *C12Y 207/07009* (2013.01); *C12Y 503/01009* (2013.01)

(58) Field of Classification Search
CPC .......................... C08B 37/0072; C12N 9/0006; C12N 9/1051; C12N 9/1241; C12N 9/92; C12N 15/635; C12N 1/20; C12N 15/75; C12P 19/26; C12Y 101/01022; C12Y 204/01212; C12Y 207/07009; C12Y 503/01009

See application file for complete search history.

(56) References Cited

U.S. PATENT DOCUMENTS

2003/0175902 A1    9/2003 Sloma et al.

FOREIGN PATENT DOCUMENTS

WO    WO 99/05297 A1    2/1999

OTHER PUBLICATIONS

Chien, L. et al., "Enhanced hyaluronic acid production in Bacillus subtilis by coexpressing bacterial hemoglobin," Biotechnology Progress, Sep. 2007, vol. 23, No. 5, pp. 1017-1022.
Jongsareejit et al., "Cloning of Hyaluronan Synthase (sz-has) Gene from *Streptococcus zooepidemicus* in *Escherichia coli*", ScienceAsia, vol. 33 (2007) pp. 389-395.
Mao, Z. et al., "A recombinant *E. coli* bioprocess for hyaluronan synthesis," Applied Microbiology and Biotechnology, Springer, Berlin, DE, Mar. 24, 2009, vol. 84, No. 1, pp. 63-69.
Oudega et al., "B.subtilis genomic DNA fragment from yugL to yugP", Microbiology, vol. 143, (1997) pp. 2769-2774, GenBank accession No. Z93936, Apr. 18, 2005>.
Phan, T. T. P. et al., "Novel plasmid-based expression vectors for intra- and extracellular production of recombinant proteins in Bacillus subtilis," Protein Expression and Purification, Academic Press, San Diego, CA, US, Apr. 1, 2006, vol. 46, No. 2, pp. 189-195.
Widner, B. et al., "Hyaluronic acid production in Bacillus subtilis," Applied and Environmental Microbiology, American Society for Microbiology, US, Jul. 1, 2005, vol. 71, No. 1, pp. 3747-3752.
Yu, H. et al., "Metabolic engineering of *Escherichia coli* for biosynthesis of hyaluronic acid," Metabolic Engineering, Academic Press, US, Dec. 24, 2007, vol. 10. No. 1, pp. 24-32.
Zhang et al., "High-Level Expression and Secretion of Methyl Parathion Hydrolase in Bacillus subtilis WB800", Applied and Environmental Microbiology, vol. 71, No. 7 (2005) pp. 4101-4103.

*Primary Examiner* — Delia Ramirez
(74) *Attorney, Agent, or Firm* — Birch, Stewart, Kolasch & Birch, LLP

(57) ABSTRACT

The present invention relates to a method for the production of hyaluronic acid (HA) in *Bacillus subtilis* and *Escherichia coli* through plasmid vectors wherein the gene is under the control of strong promoter P$_{grac}$, and a system for the selection of stable bacterial strains for the production of high levels of hyaluronic acid.

12 Claims, 6 Drawing Sheets

Expression of HAS1 and TUAD in E. coli TOP-10

Cells with plasmid HT01 incorporated are larger than cells with BS5 (growth difficulties)

Cells with BS5 incorporated are yellower than the parental cells

TuaD expression in E. coli BL21 DE3

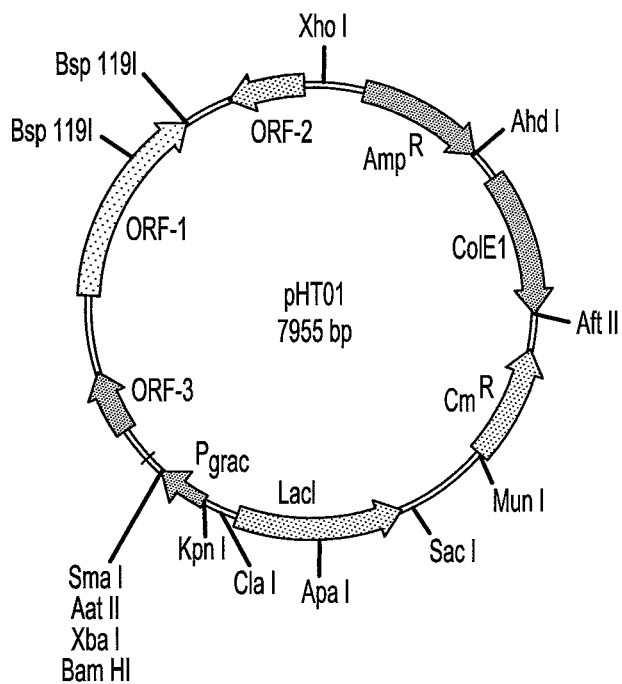

2.1. VECTOR MAP pHT01

Pgrac: Pgrac promoter (consisting of the geoE promoter; the lacO operator and the gsiB SD sequence)
ColE1 ori: Cole1 origin
Amp$^R$: ampicillin resistance
lacI: lacI gene (lac repressor)
Cm$^R$: chloramphenicol resistance Complete DNA sequence is available on request.

gaaaagaatgatgtaagcgtgaaaaattttttatcttatcac
TTGAAAttggaagggagattcttTATTATaagaattgt
  -35                             -10
ggAATTGTGAGCGGATAACAATTcccaatt
              lacO
aaaggaggaaggatcctctagagtcgacgtccccggggcagcc
  RBS    BamHI  XbaI    AatII  SmaI

Fig. 3

*Constitutive expression of hyaluronan synthase (Streptc) in E. coli*

The encoded protein, designated seHAS, is 417 amino acids long (calculated molecular weight, 47.778; calculated pI, 9.1) and is the smallest member of the HAS family identified thus far. The enzyme migrates anomalously fast in SDS-polyacrylamide gel electrophorosis (~42,000 Da).

Expression of hyaluronic acid on plates

The large, translucent colonies produce HA

Stability of the plasmid after growth

Chloramphenicol+          Chloramphenicol-

US 10,017,802 B2

PROCESS FOR THE PRODUCTION OF HYALURONIC ACID IN *ESCHERICHIA COLI* OR *BACILLUS SUBTILIS*

This application is a Divisional of copending application Ser. No. 13/821,947 (now U.S. Pat. No. 9,290,785), filed on Apr. 9, 2013, which was filed as PCT International Application No. PCT/EP2011/065642 on Sep. 9, 2011, which claims the benefit under 35 U.S.C. § 119(a) to Patent Application No. MI2010A001642, filed in ITALY on Sep. 9, 2010, all of which are hereby expressly incorporated by reference into the present application.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2015_10_21_0471_0323 PUS1_ST25.txt" created on Oct. 21, 2015, and is 17,029 bytes in size. The sequence listing contained in this .txt file is part of the specification and is hereby incorporated by reference herein in its entirety

SUBJECT OF THE INVENTION

The present invention discloses a method for the production of hyaluronic acid (HA) in *Bacillus subtilis* and *Escherichia coli* through plasmid vectors wherein the gene is under the control of the strong promoter Pgrac, and a system for the selection of stable bacterial strains, for the production of high levels of HA.

FIELD OF INVENTION

Hyaluronic acid is a natural linear polysaccharide which consists of alternating β-1-4 D-glucuronic acid and β-1-3 N-acetyl glucosamine. Hyaluronic acid is part of the glycosaminoglycan family, and can reach the molecular weight of $10^7$ Da, with approx. 300000 repeating saccharide units. It is widely distributed in the extracellular matrix of connective tissue and in the epithelium of eukaryotic organisms, where it is located on the cell surface, but can also be synthesised in some prokaryotic organisms, such as those of the *Streptococcus* family. Glycosaminoglycans are ideal joint lubricants, but also perform many other functional roles in tissue repair, adherence, development, cell motility, cancer and angiogenesis. Products based on hyaluronic acid have been developed on the basis of these important characteristics, and are used in orthopaedics, rheumatology and dermatology.

The most common natural sources of HA include rooster combs, the classic material from which HA is extracted, and some bacteria, especially those belonging to the *Streptococcus* family. All these different sources present numerous disadvantages: hyaluronic acid obtained from rooster combs can, for example, cause allergies in humans because it is of avian origin, while HA from bacterial sources must be free of all the toxins normally present in those bacteria which can cause possibly serious immune/inflammatory reactions. The current industrial HA purification processes therefore comprise many different steps, with a consequent increase in the final costs of manufacturing the raw material. There is consequently a strongly felt need for alternative sources that eliminate all the adverse events described, while maintaining reasonable manufacturing costs. In recent years, biosynthesis pathways for the synthesis of hyaluronic acid have been clarified in detail in numerous organisms. While the genes required for hyaluronic acid synthesis which are present in eukaryotic organisms are distributed throughout the genome, in bacterial systems said genes are often present and organised in operons. For example, in *Streptococcus equi* the operon for hyaluronic acid comprises 5 genes: hasA, hasB, hasC, hasD and hasE. Sometimes, however, the genes are present in two operons: in *Streptococcus equisimilis* one operon with genes hasA, hasB and hasC is present, and another with genes hasC, hasD and hasE. The genes homologous with hasB, hasC, hasD and hasE of the Streptococci are present in many organisms, because they synthesise the enzymes necessary for the synthesis of the precursors of hyaluronic acid, D-glucuronic acid and N acetyl-D glucosamine, which are also the basic constituents of the bacterial walls. In the case of Streptococci, hyaluronan synthase (hasA, which is present in the plasma membrane) is the key enzyme for the final synthesis of hyaluronic acid because it performs two functions: it catalyses the union of D-glucuronic acid and N-acetyl-D-glucosamine, and transports the chain of newly-formed hyaluronic acid out of the cell. The study of the enzymes responsible for hyaluronic acid synthesis has allowed the development of recombinant systems in various organisms, such as *Bacillus subtilis, Lactococcus lactis, Escherichia coli* and *Agrobacterium radiobacter*. The first organism engineered to produce hyaluronic acid was *B. subtilis*, through cloning in its chromosome of an operon that carries the hasA gene from *Streptococcus* (which is missing in *Bacillus*), with the tuaD and gtaB genes of *Bacillus* (corresponding to hasB and hasC of *Streptococcus*), under the control of a constitutive promoter (US2003/175902). In this way a biosynthesis pathway was organised in operons similar to those of *Streptococcus equi*, one of the major natural producers of hyaluronic acid. However, the system thus perfected leads to the industrial production of a hyaluronic acid with a molecular weight of less than 1 MDA, with very low manufacturing yields.

*Bacillus subtilis* is a Gram-positive bacterium, classified as an obligate aerobe, normally found in soil. It is capable of forming a tough, protective endospore which enables the organism to withstand extreme environmental conditions; bacteria of the genus *Bacillus* are consequently among the most widespread micro-organisms in nature, with representatives isolated from soil and aquatic environments.

Of all the species, only a very few pathogenic ones are known, including *Bacillus anthracia*, which causes anthrax, *B. thuringiensis*, a pathogen of insects, and *Bacillus cereus*, which causes food poisoning. Conversely, *Bacillus subtilis* is considered to be a GRAS (Generally Regarded As Safe) micro-organism and, being free of endo/exotoxins, is used to manufacture substances used in the food industry (both foodstuffs and drinks), products such as enzymes, antibiotics and insecticides, and in the detergent industry. Attempts to use *Bacillus subtilis* in the production of aminoacids such as tryptophan, histidine and phenylalanine, and vitamins such as biotin, folic acids and riboflavin, have given promising results.

The main source of *Bacillus* species is soil; *B. subtilis* is a prototroph which grows at mesophilic temperatures on defined (including minimal) synthetic media, containing both glucose and other sugars as carbon source.

DETAILED DESCRIPTION OF THE INVENTION

The present invention discloses a method for the production of hyaluronic acid (HA) in *Bacillus subtilis* and

*Escherichia coli* through plasmid vectors wherein the genes for the synthesis of the enzymes necessary to the production of HA are under the control of strong promoter Pgrac, and a system for the selection of stable, engineered and secreting bacterial strains, for the production of high amounts of HA having specific weight average molecular weight (in the following indicated also simply with MW).

During the construction in *E. coli* of vectors expressing hyaluronic acid in the form of plasmids, it was discovered that the genes thus introduced (responsible for synthesising hyaluronic acid-producing enzymes) are toxic to the cell when their translation control is a strong constitutive promoter. In fact, in *E. coli* transformed with the hasA and tuaD genes, gene translation of hasA alone leads to a great reduction in the precursors of D-glucuronic acid required for the constitution of the bacterial wall, with the result that the cell dies; whereas gene translation of tuaD alone generates uncontrolled synthesis of D-glucuronic acid which, by acidifying the bacterium and depriving it of glucose (its precursor), causes its death. Conversely, the translation of both genes by bacterial polymerases leads to the synthesis/activation of the two enzymes at different times, because they require different construction times with different procedures and sites of action (for example, hasA is a transmembrane protein with different domains crossing it, so a much longer time is needed for its synthesis and correct folding than for the synthesis/activation of the tuaD enzyme). The cell can only survive when balanced quantities of the precursor enzymes and the enzyme necessary for hyaluronic acid synthesis are present. In this case, the excess D-glucuronic acid, which is toxic at high levels in the cell, is used by hyaluronan synthase (hasA) which, combining it with glucosamine, incorporates it in the nascent hyaluronic acid and exports it from the cell, thus keeping the cell alive.

The Applicant has therefore now surprisingly found that although both hasA and hasB (tuaD) are necessary for hyaluronic acid synthesis, it is essential for the two genes to work in concert, leaving the cell the time required to:
produce D-glucuronic acid at non-toxic levels and
trigger the transcription of the hasA gene in such a way that the latter is able to dispose of the high levels of D-glucuronic acid as they progressively accumulate in the cell.

In the present invention, the problems described above have been solved by:
placing the plasmid genes under the control of an inducible promoter, Pgrac, which uses the repressor lac;
improving a system of selection of stable, viable, engineered and secreting *B. subtilis* strains, wherein the hasA and tuaD enzymes are present in "balanced" amounts, thus non toxic.

It is therefore object of the present invention a process for the production of hyaluronic acid in *Escherichia coli* or *Bacillus subtilis*, preferably in *Bacillus subtilis*, comprising the following steps:
(a) culture of bacterial host cells of *Escherichia coli* that constitutively express the lac repressor, or of *Bacillus subtilis* transformed with the grac-lac system, under conditions suitable for producing hyaluronic acid, and in the presence of isopropyl-β-thio-galactopyranoside (IPTG) as inducer, wherein such bacterial host cells are characterised by being transformed with:
(i) at least one episomal plasmid vector comprising a sequence coding for the enzyme hyaluronan synthase, a sequence coding for the enzyme UDP-glucose dehydrogenase in tandem, under the control of strong inducible promoter Pgrac which uses the lac repressor, or (ii) at least one episomal plasmid vector comprising a sequence coding for the enzyme hyaluronan synthase, a sequence coding for the enzyme UDP-glucose dehydrogenase, a sequence coding for the enzyme UDP-glucose pyrophosphorylase and a sequence coding for the enzyme glucose 6 phosphate isomerase, under the control of strong inducible promoter Pgrac which uses the lac repressor;
(b) recovery of hyaluronic acid from the culture medium;
wherein said bacterial host cells of *Escherichia coli* or *Bacillus subtilis* transformed with plasmid vector (i) or (ii) capable of producing hyaluronic acid of step a) are preselected in the plate on IPTG gradient.

The Applicant preferably used *B. subtilis* for its transformation with the episomal plasmid containing the genes for HA synthesis, because it presents various advantages as host for the expression of heterologous DNA:
the HA produced is easily secreted;
it is free of exotoxins and endotoxins, unlike gram-negative bacteria. Preferably said bacterial host cells of *B. subtilis* pertain to WB800N or 1012 strains.

In particular, when bacterial host cells of *B. subtilis* are used, the episomal plasmid (i) or (ii) further comprises a sequence coding for the lac repressor.

The grac-lac system transferred to *B. subtilis* (and *E. coli*) with episomal plasmid, controls the expression of the genes responsible for synthesis of the HA biosynthesis pathway (cloned in the same episomal plasmid), and guarantees very high activity and selectivity of gene transcription, leading to high production of the recombinant proteins required for the synthesis of hyaluronic acid. The final yield of the desired product will be very high, much higher than that obtained with *B. subtilis*, where the operon system is cloned on the chromosome of the bacterium and is under the control of non-inducible constitutive promoters.

In fact, the system described above is inducible: it is introduced artificially into the bacterium and activated by the Applicant by adding substances such as IPTG (isopropylthiogalactoside) in quantities of between 0.005 and 10 mM, preferably of between 0.01 and 5 mM, and more preferably between 0.4 and 1 mM.

The grac-lac system comprises the Pgrac promoter with the gene sequence LacI for the synthesis not inducible of the lac repressor protein. Pgrac is an artificial promoter comprising groE promoter, lacO operator and a ribosome binding site. IPTG (when added) determines the detachment of the lac repressor protein from the lacO operator site, so that the *B. subtilis* polymerase can recognise the groE promoter and starts the transcription of hasA and tuaD genes.

In this way, by modulating with IPTG the induction of the above disclosed system, the Applicant can control the synthesis of the whole biosynthesis process for the production of HA and obtain the wished weight average molecular weights, comprised in a range of from 100 KD to above 2 MD, with high HA yields. More particularly, when the process according to the invention uses bacterial host cells of *B. subtilis* and fermentation time is comprised of from 80 to 160 hours, it is possible to obtain HA having a weight average MW comprised in the range 100-500 KD; when fermentation time is comprised of from 40 to 80 hours, it is possible to obtain HA having a weight average MW comprised in the range 500-1000 KD; when fermentation time is comprised of from 12 to 40 hours, it is possible to obtain HA having a weight average MW comprised in the range $1 \times 10^6$-$2 \times 10^6$ D.

In a preferred embodiment of the present invention, the sequence coding for the enzyme hyaluronan synthase (hasA) is obtained from a *Streptococcus* strain, preferably from Streptococcus zooepidemicus, and the sequences coding for enzymes UDP-glucose dehydrogenase (hasB or tuaD), UDP-glucose pyrophosphorylase (hasC or gtaB) and glucose 6 phosphate isomerase (hasE or pgi), are derived from B. subtilis.

According to a particularly preferred embodiment of the present invention, the sequences coding for enzymes hyaluronan synthase, UDP-glucose dehydrogenase, UDP-glucose pyrophosphorylase and glucose 6 phosphate isomerase include an upstream Shine-Dalgarno sequence.

Even more preferably, said plasmid vector (i) comprises or consists of the nucleotide sequence as defined in SEQ ID NO:1.

The subsequent purification of the HA secreted will be extremely simple, with the result that the industrial production process will be much cheaper than the process according to the state of the art.

A further object of the present invention are plasmid vectors containing the two genes hasA and tuaD or the four genes hasA, tuaD, gtaB and pgi (corresponding to hasE), preferably plasmid vectors with two genes hasA and tuaD, under control of strong inducible promoter Pgrac, which allow the production of hyaluronic acid with high yields according to the methodology described above. In a particularly preferred embodiment of the present invention, said plasmid vector also includes a sequence coding for the lac repressor. Preferably, said sequence coding for enzyme hyaluronan synthase is gene hasA from Streptococcus zooepidemicus and said sequence coding for enzyme UDP-glucose dehydrogenase is gene tuaD from Bacillus subtilis. In a particularly preferred form, the plasmid vector comprises or consists of SEQ ID NO:1.

Preferably, the sequences coding for the hyaluronan synthase enzyme, UDP-glucose dehydrogenase, UDP-glucose pyrophosphorylase and glucose 6 phosphate isomerase include an upstream Shine-Dalgarno sequence. These vectors can also be constructed so as to contain any other gene relating to the biosynthesis of hyaluronic acid. Unlike those available to date, the starting plasmid is small, which allows engineering of the entire hyaluronic acid biosynthesis pathway (i.e. the two genes hasA and tuaD or the four genes hasA, tuaD, gtaB and pgi) in a single plasmid, which is called pHT01hasAtuaD or pHT01hasAtuaDgtaBpgi here, making the invention described economically advantageous and successfully applicable on an industrial scale. A further subject of the present invention is consequently plasmid pHT01hasAtuaD and plasmid pHT01hasAtuaDgtaBpgi. For the high yield synthesis of HA having the wished high weight average molecular weight, the Applicant has demonstrated that it is preferred the engineering of B. subtilis with plasmid pHT01hasAtuaD.

The present invention also relates to a method and relative system for the production/construction of bacterial strains, transformed with plasmid containing the entire hyaluronic acid biosynthesis pathway, and the selection of stable, viable, replicating and HA-secreting bacterial strains.

Said method comprises the following steps:
Cloning of the tuaD gene (UDP-glucose dehydrogenase) from Bacillus Subtilis,
Cloning of the hasA (hyaluronan synthase) gene from Streptococcus zooepidemicus
Construction of plasmid pGEM4hasA and subsequently of plasmid pHT01hasA
Construction of plasmid with the tuaD gene following hasA
Construction of plasmid pHT01hasAtuaD, which will be referred to as pBS5

Transformation of plasmid pBS5 into Bacillus subtilis or E. coli
Selection of cells secreting hyaluronic acid through IPTG gradient
Selection of stable, viable and secreting cells.

The present invention will be now disclosed by way of example but not of limitation, according to preferred embodiments with particular reference to the attached figures, wherein:

FIG. 3 (SEQ ID NO: 12) illustrates the vector map pHT01 comprising Pgrac promoter consisting of the groE promoter, the lacO operator and the gsB SD sequence; the replication origin ColE1; $Amp^R$ ampicillin resistance gene; lad gene (lad repressor); and $Cm^R$ chloramphenicol resistance gene;

Figure 4:
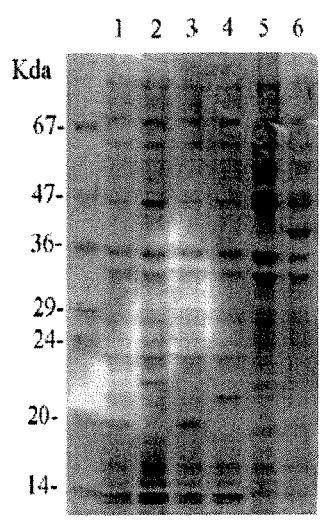
Figure 5:
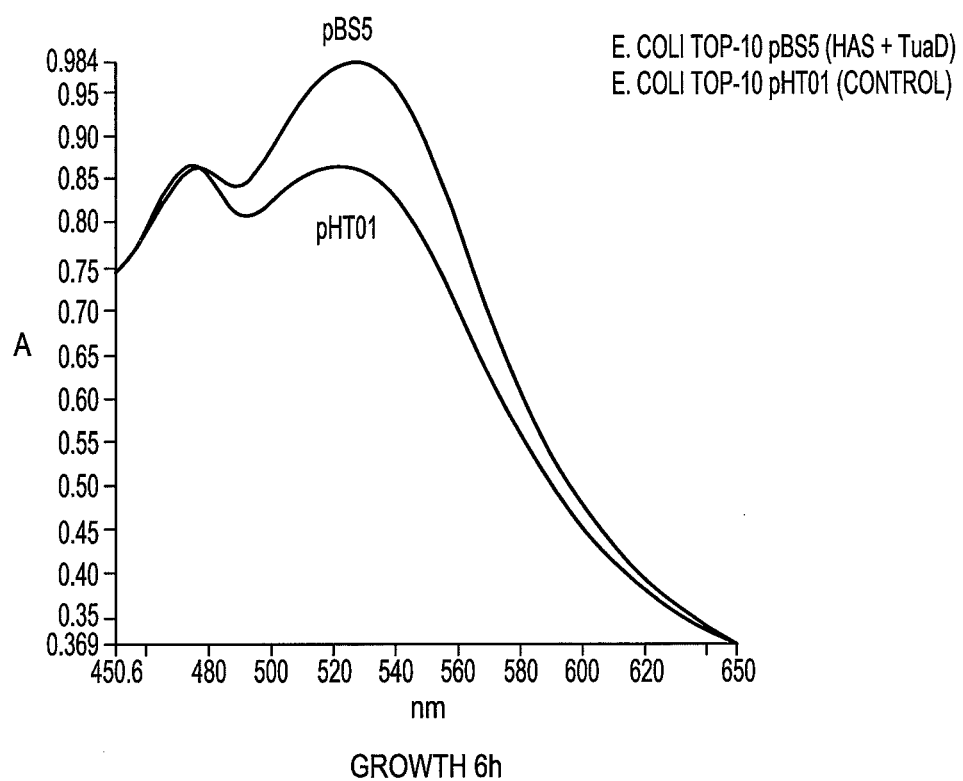
Figure 6:
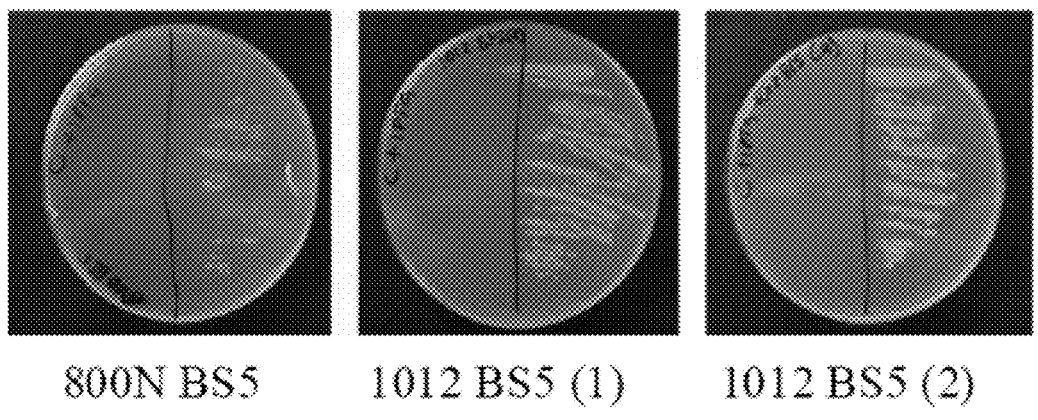
Figure 7:
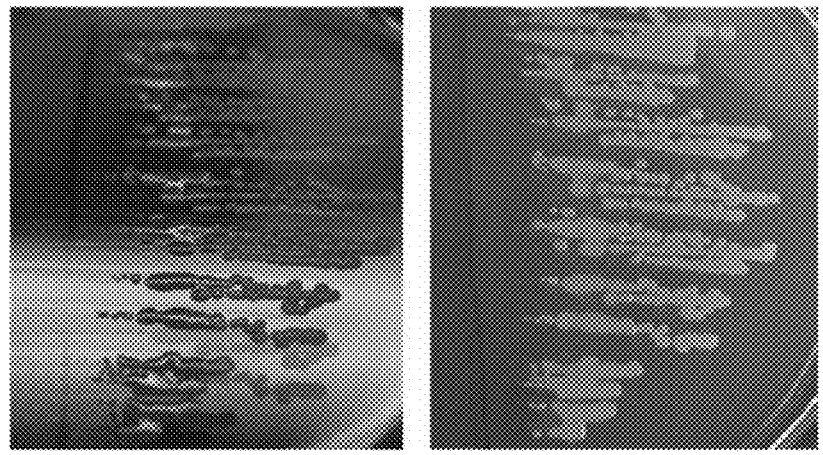
Figure 8:
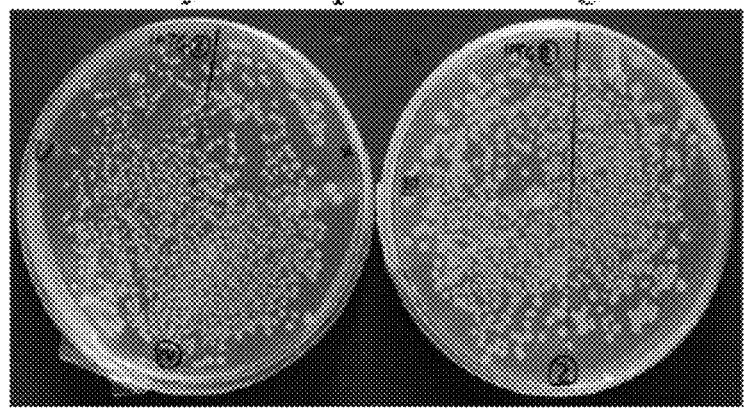

FIG. 4 shows the analysis in gel electrophoresis of the constitutive expression of hyaluronan synthase (Strept) in E. coli; the encoded protein designated SeHAS is 417 amino acids long (calculated molecular weight 47,778; calculated PI 9.1) and is the smallest member of the HAS family identified thus far; the enzyme migrates anomalously fast in SDS polyacrylamide gel electrophoresis (about 42000 Da);

FIG. 5 shows the comparison between the profiles of expression of HA in strains of E. Coli TOP10+pBS5 (hasA+ tuaD) and TOP10+pHT01 (control) through carbazole analysis of glucuronic acid at 530 nm;

FIG. 6 shows the comparison in plates among the expression of glucuronic acid in strains of Bacillus subtilis WB800N and 1012 transformed with pBS5; when bacteria are seeded in presence of IPTG 1 mM, they die because tuaD expressed at high amounts in B. subtilis is toxic;

FIG. 7 shows the expression of glucuronic acid in Bacillus subtilis in plates wherein large and translucent colonies produce HA;

FIG. 8 shows the results of plating assays to verify the stability of plasmid after 24 hours of cells growth in presence of IPTG and saccharose and in presence or absence of chloramphenicol.

The following examples describe the various steps required for the embodiment of the process of production of HA according to the present invention, by way of example but not of limitation.

Example 1

Cloning of the tuaD Gene (UDP-Glucose Dehydrogenase) from Bacillus Subtilis

The sequence of the tuaD gene, which is 9300 bp long in B. subtilis, is present in the databases as access number AF015609; it codes for the operon which leads to teichuronic acid synthesis and comprises 8 genes, tuaAB-CDEFGH. In our case the gene of interest tuaD falls between the bases 3582-4984 bp. Software analysis for restriction enzymes indicates that the restriction sites ClaI, EcoRI, PstI, HindIII and SphI are present, and therefore cannot be used for cloning. The start codon is not a methionine but a valine; in the present invention it was replaced with the codon for methionine, which translates the protein much more efficiently. Two oligonucleotide primers synthesised with the following sequence were used to recover this sequence:

```
                                                (SEQ ID NO: 2)
    5' atgaaaaaatagctgtcattggaacag 3'
    and (SEQ ID NO: 3)
    5' ttataaattgtcgttcccaagtct 3'
```

The genomic DNA from *B. subtilis* (strain 168) was obtained with the Qiagen extraction kit. With 32 cycles of PCR, using DNA from *B. subtilis* as template and the two said oligonucleotides, an amplificate of the expected molecular weight was obtained. The amplificate obtained was tested for the presence of restriction enzyme EcoRI. After cutting with this enzyme in 1% agarose gel, two bands of DNA weighing 470 bp and 920 bp are present, which correspond to those expected. To clone the tuaD gene in an expression vector, two other oligonucleotides with the following sequence were synthesised:

```
                                                (SEQ ID NO: 4)
    5' gctggatccatgaaaaaatagctgtcattgg 3'
    and (SEQ ID NO: 5)
    5' ctcgctagcttataaattgacgcttcccaag 3'
``` so as to insert said sequence between the restriction sites BamHI and NheI in the expression vector, plasmid pRSETB (INVITROGEN).

A Shine-Dalgarno (SD) sequence needs to be introduced into the tuaD gene upstream of the 5' end of the gene to allow efficient recognition by the bacterial RNA polymerase. For this purpose the DNA was amplified with the following oligonucleotides:

```
                                                (SEQ ID NO: 6)
    5' cgacatatgaaaaaatagctgtcattgg 3'
    and (SEQ ID NO: 7)
    5' ctcgctagcttataaattgacgcttcccaag 3'.
```

They contain in 5' two restriction sites NdeI and NheI which allow its cloning in vector pRSET B between the same sites. In this way, a particularly efficient sequence SD, which is necessary for RNA polymerase in order to synthesise the protein, is present upstream of the NdeI restriction site of plasmid pRSET B. Restriction site XbaI, which will be required for the subsequent clonings, is also present even before said sequence. The vector created, pRSET B, was therefore called pRSEtuaD.

Thus in this plasmid, the sequence coding for tuaD falls between the restriction sites NdeI and NheI; restriction site XbaI, which is necessary for the subsequent cloning, is present before and upstream of said plasmid, and other restriction sites, including BamHI--BglII--XhoI, are present behind the tuaD gene.

The diagram below summarises the sites of interest present in plasmid pRSEtuaD

XbaI--NdeI----------------tuaD----------------NheI-BamHI--BglI-XhoI

Figure 1:
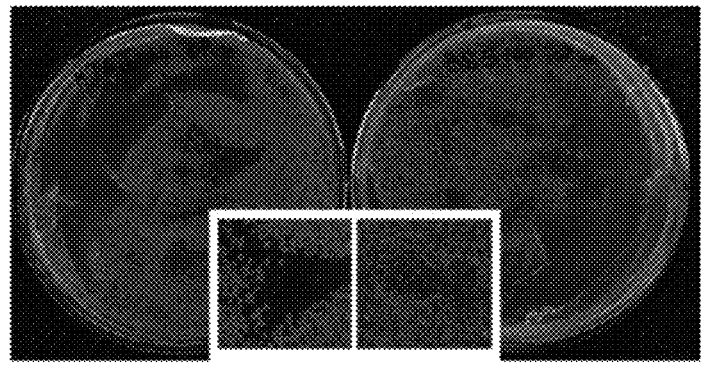
FIG. 1 shows a comparison in plates between the growth of cells E. coli TOP10, incorporating plasmid pHT01 (control) and cells E. coli TOP10, incorporating pBS5 (hasA+ tuaD)

The plasmid described is an expression vector which also functions in *E. coli*, because the gene is under the control of the T7 promoter; if it is transformed to bacterial cells BL21 DE3, which are able to transcribe T7 RNA polymerase, it therefore enables them to express the tuaD gene. After induction with 1 mM of IPTG the transfected cells are able to produce the protein of the expected molecular weight, but not hyaluronic acid. The construction is particularly efficient because the level of expression is very high. The sizes of the colonies which carry plasmid pRSEtuaD are very small compared with the control cells (FIG. 1), which demonstrates the toxicity of the tuaD gene. This cloning is difficult precisely because it is apparently difficult for the colonies to grow; the particularly high level of expression of this protein probably drains the glucose available for uncontrolled synthesis of D-glucuronic acid, thus depriving the cell of its main energy source. The cells in which the tuaD synthesis is induced with IPTG are unable to survive for a long time, so the gene product is toxic.

Figure 2:
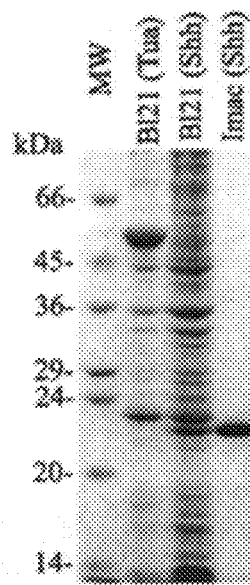
FIG. 2 shows the gel analysis of the expression of gene tuaD in E. coli BL21 DE3.

In conclusion, the tuaD gene was isolated and cloned in a plasmid and the sequence proved correct. The gene expressed in *E. coli* is able to produce a protein of the expected molecular weight corresponding to that described for tuaD (54 kDa, FIG. 2); however, in the absence of hyaluronan synthase, these cells are unable to produce significant amounts of hyaluronic acid, and the consequent accumulation of glucuronate is toxic to the cell.

Example 2

Cloning of the hasA (Hyaluronan Synthase) Gene from *Streptococcus zooepidemicus*

The gene sequence for hyaluronan synthase is present in the databases with access number AY173078, and is 3552 bp long; the sequence coding for the protein is between bases 1 and 1254. The restriction sites HindIII and StuI are present in this sequence, and therefore cannot be used for cloning, but can be used to verify the cloning. Two oligonucleotides for use with PCR were designed and synthesised to recover the coding sequence:

```
                                                (SEQ ID NO: 8)
    5' atgagaacattaaaaaacctcataac 3' e (SEQ ID NO: 9)
    5' taataatttttacgtgttccccag 3'
```

The genomic DNA from the bacterium *Streptococcus zooepidemicus* was recovered with the Qiagen extraction kit. The 1254 bp coding sequence was recovered with PCR. The expected amplificate of the correct dimensions was controlled with restriction enzyme HindIII, and gave rise to two bands of approx. 100 bp and 1150 bp which correspond to the expected cut.

Example 3

Construction of Expression Plasmid pHT01hasA for *Bacillus subtilis*

To clone said gene in expression vector pHT01 (Mobitec—FIG. 3) containing the gene promoter-repressor system grac-lac, the above-mentioned sequence must be cloned between restriction sites BamHI and XbaI. Two other oligonucleotides with the following sequence were created for this purpose:

```
                                                (SEQ ID NO: 10)
    5' ggaggatccatgagaacattaaaaaacctcat 3' e (SEQ ID NO: 11)
    5' cagtctagattataataattttttacgtgtcc 3'
```

In the first oligonucleotide, restriction site BamHI was created near 5', while in the second oligonucleotide, restriction site XbaI was created, again at 5'. The amplificate obtained through these two oligonucleotides was cloned in plasmid pGEM4Z (PROMEGA) between restriction sites BamHI and XbaI to give plasmid pGEM4hasA.

The DNA sequence between said two restriction sites was analysed with an ABI 7000 sequencer, and proved correct.

HindIII-BamHI----------------hasA----------------XbaI-SalI

The plasmid was checked for expression of the recombinant protein in *E. coli*, and presented a molecular weight of approx. 42 kDa (which agrees with the weight reported for that protein in the literature, although it has a theoretical molecular weight of 47.778 kDa, FIG. 4).

To clone said sequence between restriction sites BamHI and XbaI of vector pHT01, plasmid pGEM4hasA was cut in sites BamHI and XbaI, and the 1240 bp band was cloned in the same sites as plasmid pHT01 to obtain plasmid pHT01hasA. This plasmid is unable to produce significant quantities of hyaluronic acid because it lacks the tuaD gene. This proves that the presence of hasA alone is not sufficient to express significant amounts of HA.

Example 4

Construction of Expression Plasmid pHT01hasA-tuaD for *Bacillus subtilis*

With this construction, the hasA gene is placed in tandem with the tuaD gene under the control of inducible promoter Pgrac present in plasmid pHT01 (Mobitec). Plasmid pGEM4hasA (described in the previous example) was used as vector for this purpose, as it already contains the hasA gene. Said plasmid was cut in sites XbaI and SalI, while the sequence of the tuaD gene was cut by plasmid pRESEtuaD in sites XbaI and XhoI and then cloned in the same sites (XhoI and SalI are compatible).

pGEM4hasA
HindIII-BamHI----------------hasA----------------XbaI-SalI
pRSEtuaD
XbaI--NdeI----------------tuaD----------------NheI-BamHI--BglI-XhoI obtaining this sequence:

HindIII-BamHI---------hasA---------XbaI--NdeI---------tuaD-----------NheI-BamHI--BglI-XhoI At this point the hasA gene is in tandem with the tuaD gene; fragment BamHI----NheI, which is obtained from the plasmid by cutting with said restriction enzymes, contains the hasA gene and the tuaD gene in tandem. The fragment was then cloned in vector pHT01 between restriction sites BamHI and XbaI (XbaI is compatible with NheI), giving rise to plasmid pBS5, the complete, controlled sequence of which is set out below:

(SEQ ID NO: 1)

```
   0  TTAAGTTATTGGTATGACTGGTTTTAAGCGCAAAAAAAGTTGCTTTTTCGTACCTATTAA
  60  TGTATCGTTTTAGAAAACCGACTGTAAAAAGTACAGTCGGCATTATCTCATATTATAAAA
 120  GCCAGTCATTAGGCCTATCTGACAATTCCTGAATAGAGTTCATAAACAATCCTGCATGAT
 180  AACCATCACAAACAGAATGATGTACCTGTAAAGATAGCGGTAAATATATTGAATTACCTT
 240  TATTAATGAATTTTCCTGCTGTAATAATGGGTAGAAGGTAATTACTATTATTATTGATAT
 300  TTAAGTTAAACCCAGTAAATGAAGTCCATGGAATAATAGAAAGAGAAAAAGCATTTTCAG
 360  GTATAGGTGTTTTGGGAAACAATTTCCCCGAACCATTATATTTCTCTACATCAGAAAGGT
 420  ATAAATCATAAAACTCTTTGAAGTCATTCTTTACAGGAGTCCAAATACCAGAGAATGTTT
 480  TAGATACACCATCAAAAATTGTATAAAGTGGCTCTAACTTATCCCAATAACCTAACTCTC
 540  CGTCGCTATTGTAACCAGTTCTAAAAGCTGTATTTGAGTTTATCACCCTTGTCACTAAGA
 600  AAATAAATGCAGGGTAAAATTTATATCCTTCTTGTTTTATGTTTCGGTATAAAACACTAA
 660  TATCAATTTCTGTGGTTATACTAAAAGTCGTTTGTTGGTTCAAATAATGATTAAATATCT
 720  CTTTTCTCTTCCAATTGTCTAAATCAATTTTATTAAAGTTCATTTGATATGCCTCCTAAA
 780  TTTTTATCTAAAGTGAATTTAGGAGGCTTACTTGTCTGCTTTCTTCATTAGAATCAATCC
 840  TTTTTTAAAAGTCAATATTACTGTAACATAAATATATATTTTAAAAATATCCCACTTTAT
 900  CCAATTTTCGTTTGTTGAACTAATGGGTGCTTTAGTTGAAGAATAAAGACCACATTAAAA
 960  AATGTGGTCTTTTGTGTTTTTTTAAAGGATTTGAGCGTAGCGAAAAATCCTTTTCTTTCT
1020  TATCTTGATAATAAGGGTAACTATTGCCGATCGTCCATTCCGACAGCATCGCCAGTCACT
```

```
                                            -continued
1080  ATGGCGTGCTGCTAGCGCCATTCGCCATTCAGGCTGCGCAACTGTTGGGAAGGGCGATCG 1140  GTGCGGGCCTCTTCGCTATTACGCCAGCTGGCGAAAGGGGATGTGCTGCAAGGCGATTA
                                                               EcoRI
1200  AGTTGGGTAACGCCAGGGTTTTCCCAGTCACGACGTTGTAAAACGACGGCCAGTGAATTC

1260  GAGCTCAGGCCTTAACTCACATTAATTGCGTTGCGCTCACTGCCCGCTTTCCAGTCGGGA

1320  AACCTGTCGTGCCAGCTGCATTAATGAATCGGCCAACGCGCGGGGAGAGGCGGTTTGCGT

1380  ATTGGGCGCCAGGGTGGTTTTTCTTTTCACCAGTGAGACGGGCAACAGCTGATTGCCCTT

1440  CACCGCCTGGCCCTGAGAGAGTTGCAGCAAGCGGTCCACGCTGGTTTGCCCCAGCAGGCG

1500  AAAATCCTGTTTGATGGTGGTTGACGGCGGGATATAACATGAGCTGTCTTCGGTATCGTC

1560  GTATCCCACTACCGAGATATCCGCACCAACGCGCAGCCCGGACTCGGTAATGGCGCGCAT

1620  TGCGCCCAGCGCCATCTGATCGTTGGCAACCAGCATCGCAGTGGGAACGATGCCCTCATT

1680  CAGCATTTGCATGGTTTGTTGAAAACCGGACATGGCACTCCAGTCGCCTTCCCGTTCCGC

1740  TATCGGCTGAATTTGATTGCGAGTGAGATATTTATGCCAGCCAGCCAGACGCAGACGCGC

1800  CGAGACAGAACTTAATGGGCCCGCTAACAGCGCGATTTGCTGGTGACCCAATGCGACCAG

1860  ATGCTCCACGCCCAGTCGCGTACCGTCTTCATGGGAGAAAATAATACTGTTGATGGGTGT

1920  CTGGTCAGAGACATCAAGAAATAACGCCGGAACATTAGTGCAGGCAGCTTCCACAGCAAT

1980  GGCATCCTGGTCATCCAGCGGATAGTTAATGATCAGCCCACTGACGCGTTGCGCGAGAAG

2040  ATTGTGCACCGCCGCTTTACAGGCTTCGACGCCGCTTCGTTCTACCATCGACACCACCAC

2100  GCTGGCACCCAGTTGATCGGCGCGAGATTTAATCGCCGCGACAATTTGCGACGGCGCGTG

2160  CAGGGCCAGACTGGAGGTGGCAACGCCAATCAGCAACGACTGTTTGCCCGCCAGTTGTTG

2220  TGCCACGCGGTTGGGAATGTAATTCAGCTCCGCCATCGCCGCTTCCACTTTTTCCCGCGT

2280  TTTCGCAGAAACGTGGCTGGCCTGGTTCACCACGCGGGAAACGGTCTGATAAGAGACACC

2340  GGCATACTCTGCGACATCGTATAACGTTACTGGTTTCATCAAAATCGTCTCCCTCCGTTT

2400  GAATATTTGATTGATCGTAACCAGATGAAGCACTCTTTCCACTATCCCTACAGTGTTATG

2460  GCTTGAACAATCACGAAACAATAATTGGTACGTACGATCTTTCAGCCGACTCAAACATCA

2520  AATCTTACAAATGTAGTCTTTGAAAGTATTACATATGTAAGATTTAAATGCAACCGTTTT

2580  TTCGGAAGGAAATGATGACCTCGTTTCCACCGGAATTAGCTTGGTACCAGCTATTGTAAC

2640  ATAATCGGTACGGGGGTGAAAAAGCTAACGGAAAAGGGAGCGGAAAAGAATGATGTAAGC

2700  GTGAAAAATTTTTTATCTTATCACTTGAAATTGGAAGGGAGATTCTTTATTATAAGAATT
                                                              BamHI
2760  GTGGAATTGTGAGCGGATAACAATTCCCAATTAAAGGAGGAAGGATCCATGAGAACATTA
   1                                                        M  R  T  L

2820  AAAAACCCTCATAACTGTTGTGGCCTTTAGTATTTTTGGGTACTGTTGATTTACGTCAAT
   1   K  N  L  I  T  V  V  A  F  S  I  F  W  V  L  L  I  Y  V  N
                                         HindIII
2880  GTTTATCTCTTTGGTGCTAAAGGAAGCTTGTCAATTTATGGCTTTTTGCTGATAGCTTAC
   1   V  Y  L  F  G  A  K  G  S  L  S  I  Y  G  F  L  L  I  A  Y 2940  CTATTAGTCAAAATGTCCTTATCCTTTTTTTACAAGCCATTTAAGGGAAGGGCTGGGCAA
   1   L  L  V  K  M  S  L  S  F  F  Y  K  P  F  K  G  R  A  G  Q
```

-continued

```
3000  TATAAGGTTGCAGCCATTATTCCCTCTTATAACGAAGATGCTGAGTCATTGCTAGAGACC
   1   Y  K  V  A  A  I  I  P  S  Y  N  E  D  A  E  S  L  L  E  T

3060  TTAAAAAGTGTTCAGCAGCAAACCTATCCCCTAGCAGAAATTTATGTTGTTGACGATGGA
   1   L  K  S  V  Q  Q  Q  T  Y  P  L  A  E  I  Y  V  V  D  D  G

3120  AGTGCTGATGAGACAGGTATTAAGCGCATTGAAGACTATGTGCGTGACACTGGTGACCTA
   1   S  A  D  E  T  G  I  K  R  I  E  D  Y  V  R  D  T  G  D  L

3180  TCAAGCAATGTCATTGTTCACCGGTCAGAAAAAAATCAAGGAAAGCGTCATGCACAGGCC
   1   S  S  N  V  I  V  H  R  S  E  K  N  Q  G  K  R  H  A  Q  A

3240  TGGGCCTTTGAAAGATCAGACGCTGATGTCTTTTTGACCGTTGACTCAGATACTTATATC
   1   W  A  F  E  R  S  D  A  D  V  F  L  T  V  D  S  D  T  Y  I

3300  TACCCTGATGCTTTAGAGGAGTTGTTAAAAACCTTTAATGACCCAACTGTTTTTGCTGCG
   1   Y  P  D  A  L  E  E  L  L  K  T  F  N  D  P  T  V  F  A  A

3360  ACGGGTCACCTTAATGTCAGAAATAGACAAACCAATCTCTTAACACGCTTGACAGATATT
   1   T  G  H  L  N  V  R  N  R  Q  T  N  L  L  T  R  L  T  D  I

3420  CGCTATGATAATGCTTTTGGCGTTGAACGAGCTGCCCAATCCGTTACAGGTAATATTCTC
   1   R  Y  D  N  A  F  V  E  R  A  A  A  Q  S  V  T  G  N  I  L

3480  GTTTGCTCAGGCCCGCTTAGCGTTTACGACGCGAGGTGGTTGTTCCTAACATAGATAGA
   1   V  C  S  G  P  L  S  V  Y  R  R  E  V  V  V  P  N  I  D  R

3540  TACATCAACCAGACCTTCCTGGGTATTCCTGTAAGTATCGGTGATGACAGGTGCTTGACC
   1   Y  I  N  Q  T  F  L  G  I  P  V  S  I  G  D  D  R  C  L  T

3600  AACTATGCAACTGATTTAGGAAAGACTGTTTATCAATCCACTGCTAAATGTATTACAGAT
   1   N  Y  A  T  D  L  G  K  T  V  Y  Q  S  T  A  K  C  I  T  D

3660  GTTCCTGACAAGATGTCTACTTACTTGAAGCAGCAAAACCGCTGGAACAAGTCCTTCTTT
   1   V  P  D  K  M  S  T  Y  L  K  Q  Q  N  R  W  N  K  S  F  F

3720  AGAGAGTCCATTATTTCTGTTAAGAAAATCATGAACAATCCTTTTGTAGCCCTATGGACC
   1   R  E  S  I  I  S  V  K  K  I  M  N  N  P  F  V  A  L  W  T

3780  ATACTTGAGGTGTCTATGTTTATGATGCTTGTTTATTCTGTGGTGGATTTCTTTGTAGGC
   1   I  L  E  V  S  M  F  M  M  L  V  Y  S  V  V  D  F  F  V  G

3840  AATGTCAGAGAATTTGATTGGCTCAGGGTTTTGGCCTTTCTGGTGATTATCTTCATTGTT
   1   N  V  R  E  F  D  W  L  R  V  L  A  F  L  V  I  I  F  I  V

3900  GCTCTTTGTCGTAATATTCACTATATGCTTAAGCACCCGCTGTCCTTCTTGTTATCTCCG
   1   A  L  C  R  N  I  H  Y  M  L  K  H  P  L  S  F  L  L  S  P

3960  TTTTATGGGGTACTGCATTTGTTTGTCCTACAGCCCTTGAAATTGTATTCTCTTTTTACT
   1   F  Y  G  V  L  H  L  F  V  L  Q  P  L  K  L  Y  S  L  F  T
                                                            XbaI
4020  ATTAGAAATGCTGACTGGGGAACACGTAAAAAATTATTATAATCTAGAAATAATTTTGTT
   1   I  R  N  A  D  W  G  T  R  K  K  L  L

4080  TAACTTTAAGAAGGAGATATACATATGAAAAAAATAGCTGTCATTGGAACAGGTTATGTA
   1                       M  K  K  I  A  V  I  G  T  G  Y  V
```

```
                                       -continued
4140  GGACTCGTATCAGGCACTTGCTTTGCGGAGATCGGCAATAAAGTTGTTTGCTGTGATATC
   1   G  L  V  S  G  T  C  F  S  I  G  N  N  K  V  V  C  C  D  I 4200  GATGAATCAAAAATCAGAAGCCTGAAAAATGGGGTAATCCCAATCTATGAACCAGGGCTT
   1   D  E  S  K  I  R  S  L  K  N  G  V  I  P  I  Y  E  P  G  L 4260  GCAGACTTAGTTGAAAAAAATGTGCTGGATCAGCGCCTGACCTTTACGAACGATATCCCG
   1   A  D  L  V  E  K  N  V  L  D  Q  R  L  T  F  T  N  D  I  P 4320  TCTGCCATTCGGGCCTCAGATATTATTTATATTGCAGTCGGAACGCCTATGTCCAAAACA
   1   S  A  I  R  A  S  D  I  I  Y  I  A  V  G  T  P  M  S  K  T 4380  GGTGAAGCTGATTTAACGTACGTCAAAGCGGCGGCGAAAACAATCGGTGAGCATCTTAAC
   1   G  E  A  D  L  T  Y  V  K  A  A  A  K  T  I  G  E  H  L  N 4440  GGCTACAAAGTGATCGTAAATAAAAGCACAGTCCCGGTTGGAACAGGGAAACTGGTGCAA
   1   G  Y  K  V  I  V  N  K  S  T  V  P  V  G  T  G  K  L  V  Q
EcoRI
4500  TCTATCGTTCAAAAAGCCTCAAAGGGGAGATACTCATTTGATGTTGTATCTAACCCTGAA
   1   S  I  V  Q  K  S  K  G  G  R  Y  S  F  D  V  V  S  N  P  E 4560  TTCCTTCGGGAAGGGTCAGCGATTCATGACACGATGAATATGGAGCGTGCCGTGATTGGT
   1   F  L  R  E  G  S  A  I  H  D  T  M  N  M  E  R  A  V  I  G 4620  TCAACAAGTCATAAAGCCGCTGCCATCATTGAGGAACTTCATCAGCCATTCCATGCTCCT
   1   S  T  S  H  K  A  A  A  I  I  E  E  L  H  Q  P  F  H  A  P 4680  GTCATTAAAACAAACCTAGAAAGTGCAGAAATGATTAAATACGCCGCGAATGCATTTCTG
   1   V  I  K  T  N  L  E  S  A  E  M  I  K  Y  A  A  N  A  F  L 4740  GCGACAAAGATTTCCTTTATCAACGATATCGCAAACATTTGTGAGCGAGTCGGCGCAGAC
   1   A  T  K  I  S  F  I  N  D  I  A  N  I  C  E  R  V  G  A  D 4800  GTTTCAAAAGTTGCTGATGGTGTTGGTCTTGACAGCCGTATCGGCAGAAAGTTCCTTAAA
   1   V  S  K  V  A  D  G  V  G  L  D  S  R  I  G  R  K  F  L  K 4860  GCTGGTATTGGATTCGGCGGTTCATGTTTTCCAAAGGATACAACCGCGCTGCTTCAAATC
   1   A  G  I  G  F  G  G  S  C  F  P  K  D  T  T  A  L  L  Q  I 4920  GCAAAATCGGCAGGCTATCCATTCAAGCTCATCGAAGCTGTCATTGAAACGAACGAAAAG
   1   A  K  S  A  G  Y  P  F  K  L  I  E  A  V  I  E  T  N  E  K 4980  CAGCGTGTTCATATTGTAGATAAACTTTTGACTGTTATGGGAAGCGTCAAAGGGAGAACC
   1   Q  R  V  H  I  V  D  K  L  L  T  V  M  G  S  V  K  G  R  T 5040  ATTTCAGTCCTGGGATTAGCCTTCAAACCGAATACGAACGATGTGAGATCCGCTCCAGCG
   1   I  S  V  L  G  L  A  F  K  P  N  T  N  D  V  R  S  A  P  A 5100  CTTGATATTATCCCAATGCTGCAGCAGCTGGGCGCCCATGTAAAAGCATACGATCCGATT
   1   L  D  I  I  P  M  L  Q  Q  L  G  A  H  V  K  A  Y  D  P  I
                     HindIII
5160  GCTATTCCTGAAGCTTCAGCGATCCTTGGCGAACAGGTCGAGTATTACACAGATGTGTAT
   1   A  I  P  E  A  S  A  I  L  G  E  Q  V  E  Y  Y  T  D  V  Y 5220  GCTGCGATGGAAGACACTGATGCATGCCTGATTTTAACGGATTGGCCGGAAGTGAAAGAA
   1   A  A  M  E  D  T  D  A  C  L  I  L  T  D  W  P  E  V  K  E
```

```
                                      -continued
5280  ATGGAGCTTGTAAAAGTGAAAACCCTCTTAAAACAGCCAGTCATCATTGACGGCAGAAAT
  1    M  E  L  V  K  V  K  T  L  L  K  Q  P  V  I  I  D  G  R  N 5340  TTATTTTCACTTGAAGAGATGCAGGCAGCCGGATACATTTATCACTCTATCGGCCGTCCC
  1    L  F  S  L  E  E  M  Q  A  A  G  Y  I  Y  H  S  I  G  R  P 5400  GCTGTTCGGGGAACGGAACCCTCTGACAAGTATTTTCCGGGCTTGCCGCTTGAAGAATTG
  1    A  V  R  G  T  E  P  S  D  K  Y  F  P  G  L  P  L  E  E  L
                                          Nhe/XbaI         SmaI
5460  GCTAAAGACTTGGGAAGCGTCAATTTATAAGCTAGAGTCGACGTCCCCGGGGCAGCCCGC
  1    A  K  D  L  G  S  V  N  L

5520  CTAATGAGCGGGCTTTTTTCACGTCACGCGTCCATGGAGATCTTTGTCTGCAACTGAAAA

5580  GTTTATACCTTACCTGGAACAAATGGTTGAAACATACGAGGCTAATATCGGCTTATTAGG

5640  AATAGTCCCTGTACTAATAAAATCAGGTGGATCAGTTGATCAGTATATTTTGGACGAAGC

5700  TCGGAAAGAATTTGGAGATGACTTGCTTAATTCCACAATTAAATTAAGGGAAAGAATAAA

5760  GCGATTTGATGTTCAAGGAATCACGGAAGAAGATACTCATGATAAAGAAGCTCTAAAACT

5820  ATTCAATAACCTTACAATGGAATTGATCGAAAGGGTGGAAGGTTAATGGTACGAAAATTA
                              HindIII
5880  GGGGATCTACCTAGAAAGCCACAAGGCGATAGGTCAAGCTTAAAGAACCCTTACATGGAT

5940  CTTACAGATTCTGAAAGTAAAGAAACAACAGAGGTTAAACAAACAGAACCAAAAAGAAAA

6000  AAAGCATTGTTGAAAACAATGAAAGTTGATGTTTCAATCCATAATAAGATTAAATCGCTG
                     EcoRI
6060  CACGAAATTCTGGCAGCATCCGAAGGGAATTCATATTACTTAGAGGATACTATTGAGAGA

6120  GCTATTGATAAGATGGTTGAGACATTACCTGAGAGCCAAAAAACTTTTTATGAATATGAA

6180  TTAAAAAAAAGAACCAACAAAGGCTGAGACAGACTCCAAACGAGTCTGTTTTTTAAAAA

6240  AAATATTAGGAGCATTGAATATATATTAGAGAATTAAGAAAGACATGGGAATAAAAATAT

6300  TTTAAATCCAGTAAAAATATGATAAGATTATTTCAGAATATGAAGAACTCTGTTTGTTTT

6360  TGATGAAAAACAAACAAAAAAAATCCACCTAACGGAATCTCAATTTAACTAACAGCGGC

6420  CAAACTGAGAAGTTAAATTTGAGAAGGGGAAAAGGCGGATTTATACTTGTATTTAACTAT

6480  CTCCATTTTAACATTTTATTAAACCCCATACAAGTGAAAATCCTCTTTTACACTGTTCCT

6540  TTAGGTGATCGCGGAGGGACATTATGAGTGAAGTAAACCTAAAAGGAAATACAGATGAAT

6600  TAGTGTATTATCGACAGCAAACCACTGGAAATAAATCGCCAGGAAGAGAATCAAAAAAG

6660  GGAAAGAAGAAGTTTATTATGTTGCTGAAACGGAAGAGAAGATATGGACAGAAGAGCAAA

6720  TAAAAAACTTTTCTTTAGACAAATTTGGTACGCATATACCTTACATAGAAGGTCATTATA

6780  CAATCTTAAATAATTACTTCTTTGATTTTTGGGGCTATTTTTTAGGTGCTGAAGGAATTG

6840  CGCTCTATGCTCACCTAACTCGTTATGCATACGGCAGCAAAGACTTTTGCTTTCCTAGTC

6900  TACAAACAATCGCTAAAAAAATGGACAAGACTCCTGTTACAGTTAGAGGCTACTTGAAAC

6960  TGCTTGAAAGGTACGGTTTTATTTGGAAGGTAAACGTCCGTAATAAAACCAAGGATAACA

7020  CAGAGGAATCCCCGATTTTTAAGATTAGACGTAAGGTTCCTTTGCTTTCAGAAGAACTTT

7080  TAAATGGAAACCCTAATATTGAAATTCCAGATGACGAGGAAGCACATGTAAAGAAGGCTT

7140  TAAAAAAGGAAAAAGAGGGTCTTCCAAAGGTTTTGAAAAAAGAGCACGATGAATTTGTTA

7200  AAAAAATGATGGATGAGTCAGAAACAATTAATATTCCAGAGGCCTTACAATATGACACAA

7260  TGTATGAAGATATACTCAGTAAAGGAGAAATTCGAAAAGAAATCAAAAAACAAATACCTA
```

```
7320  ATCCTACAACATCTTTTGAGAGTATATCAATGACAACTGAAGAGGAAAAAGTCGACAGTA
7380  CTTTAAAAAGCGAAATGCAAAATCGTGTCTCTAAGCCTTCTTTTGATACCTGGTTTAAAA
7440  ACACTAAGATCAAAATTGAAAATAAAAATTGTTTATTACTTGTACCGAGTGAATTTGCAT
7500  TTGAATGGATTAAGAAAAGATATTTAGAAACAATTAAAACAGTCCTTGAAGAAGCTGGAT
7560  ATGTTTTCGAAAAAATCGAACTAAGAAAAGTGCAATAAACTGCTGAAGTATTTCAGCAGT
7620  TTTTTTTATTTAGAAATAGTGAAAAAAATATAATCAGGGAGGTATCAATATTTAATGAGT
7680  ACTGATTTAAATTTATTTAGACTGGAATTAATAATTAACACGTAGACTAATTAAAATTTA
7740  ATGAGGGATAAAGAGGATACAAAAATATTAATTTCAATCCCTATTAAATTTTAACAAGGG
7800  GGGGATTAAAATTTAATTAGAGGTTTATCCACAAGAAAAGACCCTAATAAAATTTTTACT
7860  AGGGTTATAACACTGATTAATTTCTTAATGGGGGAGGGATTAAAATTTAATGACAAAGAA
                      HindIII
7920  AACAATCTTTTAAGAAAAGCTTTTAAAAGATAATAATAAAAAGAGCTTTGCGATTAAGCA
7980  AAACTCTTTACTTTTTCATTGACATTATCAAATTCATCGATTTCAAATTGTTGTTGTATC
8040  ATAAAGTTAATTCTGTTTTGCACAACCTTTTCAGGAATATAAAACACATCTGAGGCTTGT
8100  TTTATAAACTCAGGGTCGCTAAAGTCAATGTAACGTAGCATATGATATGGTATAGCTTCC
8160  ACCCAAGTTAGCCTTTCTGCTTCTTCTGAATGTTTTTCATATACTTCCATGGGTATCTCT
8220  AAATGATTTTCCTCATGTAGCAAGGTATGAGCAAAAAGTTTATGGAATTGATAGTTCCTC
8280  TCTTTTTCTTCAACTTTTTTATCTAAAACAAACACTTTAACATCTGAGTCAATGTAAGCA
8340  TAAGATGTTTTTCCAGTCATAATTTCAATCCCAAATCTTTTAGACAGAAATTCTGGACGT
8400  AAATCTTTTGGTGAAAGAATTTTTTTATGTAGCAATATATCCGATACAGCACCTTCTAAA
8460  AGCGTTGGTGAATAGGGCATTTTACCTATCTCCTCTCATTTTGTGGAATAAAAATAGTCA
8520  TATTCGTCCATCTACCTATCCTATTATCGAACAGTTGAACTTTTTAATCAAGGATCAGTC
8580  CTTTTTTTCATTATTCTTAAACTGTGCTCTTAACTTTAACAACTCGATTTGTTTTTCCAG
8640  ATCTCGAGGGTAACTAGCCTCGCCGATCCCGCAAGAGGCCCGGCAGTCAGGTGGCACTTT
8700  TCGGGGAAATGTGCGCGGAACCCCTATTTGTTTATTTTTCTAAATACATTCAAATATGTA
8760  TCCGCTCATGAGACAATAACCCTGATAAATGCTTCAATAATATTGAAAAAGGAAGAGTAT
8820  GAGTATTCAACATTTCCGTGTCGCCCTTATTCCCTTTTTTGCGGCATTTTGCCTTCCTGT
8880  TTTTGCTCACCCAGAAACGCTGGTGAAAGTAAAAGATGCTGAAGATCAGTTGGGTGCACG
8940  AGTGGGTTACATCGAACTGGATCTCAACAGCGGTAAGATCCTTGAGAGTTTTCGCCCCGA
9000  AGAACGTTTTCCAATGATGAGCACTTTTAAAGTTCTGCTATGTGGCGCGGTATTATCCCG
9060  TATTGACGCCGGGCAAGAGCAACTCGGTCGCCGCATACACTATTCTCAGAATGACTTGGT
9120  TGAGTACTCACCAGTCACAGAAAAGCATCTTACGGATGGCATGACAGTAAGAGAATTATG
9180  CAGTGCTGCCATAACCATGAGTGATAACACTGCGGCCAACTTACTTCTGACAACGATCGG
9240  AGGACCGAAGGAGCTAACCGCTTTTTTGCACAACATGGGGGATCATGTAACTCGCCTTGA
9300  TCGTTGGGAACCGGAGCTGAATGAAGCCATACCAAACGACGAGCGTGACACCACGATGCC
9360  TGTAGCAATGGCAACAACGTTGCGCAAACTATTAACTGGCGAACTACTTACTCTAGCTTC
9420  CCGGCAACAATTAATAGACTGGATGGAGGCGGATAAAGTTGCAGGACCACTTCTGCGCTC
9480  GGCCCTTCCGGCTGGCTGGTTTATTGCTGATAAATCTGGAGCCGGTGAGCGTGGGTCTCG
9540  CGGTATCATTGCAGCACTGGGGCCAGATGGTAAGCCCTCCCGTATCGTAGTTATCTACAC
9600  GACGGGGAGTCAGGCAACTATGGATGAACGAAATAGACAGATCGCTGAGATAGGTGCCTC
```

```
-continued
 9660  ACTGATTAAGCATTGGTAACTGTCAGACCAAGTTTACTCATATATACTTTAGATTGATTT

9720  AAAACTTCATTTTTAATTTAAAAGGATCTAGGTGAAGATCCTTTTTGATAATCTCATGAC

9780  CAAAATCCCTTAACGTGAGTTTTCGTTCCACTGAGCGTCAGACCCCGTAGAAAAGATCAA

9840  AGGATCTTCTTGAGATCCTTTTTTTCTGCGCGTAATCTGCTGCTTGCAAACAAAAAAACC

9900  ACCGCTACCAGCGGTGGTTTGTTTGCCGGATCAAGAGCTACCAACTCTTTTTCCGAAGGT

9960  AACTGGCTTCAGCAGAGCGCAGATACCAAATACTGTCCTTCTAGTGTAGCCGTAGTTAGG

10020  CCACCACTTCAAGAACTCTGTAGCACCGCCTACATACCTCGCTCTGCTAATCCTGTTACC

10080  AGTGGCTGCTGCCAGTGGCGATAAGTCGTGTCTTACCGGGTTGGACTCAAGACGATAGTT

10140  ACCGGATAAGGCGCAGCGGTCGGGCTGAACGGGGGGTTCGTGCACACAGCCCAGCTTGGA

10200  GCGAACGACCTACACCGAACTGAGATACCTACAGCGTGAGCTATGAGAAAGCGCCACGCT

10260  TCCCGAAGGGAGAAAGGCGGACAGGTATCCGGTAAGCGGCAGGGTCGGAACAGGAGAGCG

10320  CACGAGGGAGCTTCCAGGGGGAAACGCCTGGTATCTTTATAGTCCTGTCGGGTTTCGCCA

10380  CCTCTGACTTGAGCGTCGATTTTTGTGATGCTCGTCAGGGGGCGGAGCCTATGGAAAAA

10440  CGCCAGCAACGCGGCCTTTTTACGGTTCCTGGCCTTTTGCTGGCCTTTTGCTCACATGTT

10500  CTTTCCTGCGTTATCCCCTGATTCTGTGGATAACCGTATTACCGCCTTTGAGTGAGCTGA

10560  TACCGCTCGCCGCAGCCGAACGACCGAGCGCAGCGAGTCAGTGAGCGAGGAAGCGGAAGA

10620  GCGCCCAATACG
```

In this sequence the hasA gene is present between bases 2808 and 4062, and a Shine-Dalgarno sequence (GGAGGA) is correctly present before the gene to increase the efficiency of transcription. Next, the tuaD gene is present between bases 4105 bp to 5490 bp; here again, an efficient Shine-Dalgarno sequence (AGGAGA) is present before the gene. Moreover, the start codon of valine present in the tuaD gene was replaced with the more efficient methionine. The plasmid, tested for restriction enzymes HindIII and EcoRI, gives a correct restriction pattern with the following bands: 3957 bp, 1650 bp, 1522 bp, 1243 bp and 610 bp.

This vector is able to express hyaluronic acid in *Bacillus subtilis*, and also in *E. Coli*; in fact, the carbazole test performed towards cells transfected with pBS5 with respect to cells containing the vector without these sequences shows the presence of glucuronic acid (FIG. 5—peak around 530 nm), which is one of the constituents of hyaluronic acid, exclusively in the cells engineered with pBS5.

Plasmid pHT01 is a shuttle vector able to grow in both *E. coli* and *B. subtilis*. However, it has been surprisingly found that the plasmid can be grown more efficiently in *E. Coli* cell strain INV-1α than in strain TOP-10, which is much more efficient in the transformation, because it contains the constitutively expressed lac repressor.

Plasmid pBS5 contains the inducible promoter Pgrac which uses the lac repressor. Also in *E. coli*, this promoter, induced with 1 mM IPTG, allows the bacterial polymerases to code for the downstream genes for the HA synthesis. Then, the Applicant has obtained the transformation of this plasmid (to) in *E. coli* JM110 cells, bacterial cells lacking two genes, Dam and Dcm, which lead to DNA methylation at the level of recognition sequence GATC (Dam) and CCAGG CCTGG (Dcm). This DNA transferred to the *B. subtilis* cells is able to produce hyaluronic acid with a higher weight average molecular weight than that obtainable with DNA transferred in *E. coli* INV-1α strain.

Example 5

Bacterial Transformation in *Bacillus subtilis*: Media and Bacterial Strains for the Formation of Competent Cells The transfer of engineered plasmids to *Bacillus subtilis* uses the natural entry capacity of the plasmids during a given step of bacterial growth, and is consequently a natural effect. The transformations with pBS5 were performed with different bacterial strains, in particular WB800N (MOBITEC) or 1012 (MOBITEC). The first bacterial strain was developed for the expression of recombinant proteins because it lacks eight proteases which could degrade the proteins secreted in particular (the product of the hasA gene, hyaluronan synthase, is a transmembrane protein which could therefore undergo proteolysis). Strain 1012 was used as host cell for the expression of the plasmids of series pHT.

The following media are required for the transformation:
Stock Solution of Metals 1000×
2 M $MgCl_2$
0.7 M $CaCl_2$
50 mM $MnCl_2$
5 mM $FeCl_3$
1 mM $ZnCl_2$
10×S-Base
10×MM
2 g $(NH_4)_2SO_4$
14 g $K_2HPO_4$
6 g $KH_2PO_4$
add distilled water to 100 ml and autoclave
HS Medium
For 100 ml:
10 ml 10×S-base
12.5 ml 4% glucose (m/v)
5 ml 0.1% L-tryptophan (m/v)
2 ml 1% casaminoacids (m/v)
25 ml 2% yeast extract (m/v)

10 ml 8% arginine (m/v), 0.4% histidine (m/v)
10 ml 1% sodium citrate (m/v)
0.01 ml 1M MgSO$_4$
25.49 ml distilled water
LS Medium
For 100 ml:
10 ml 10×S-base
12.5 ml 4% glucose (m/v)
0.5 ml 0.1% L-tryptophan (m/v)
1 ml 1% casaminoacids (m/v)
5 ml 2% yeast extract (m/v)
0.5 ml 0.5M MgCl$_2$
0.5 ml 0.1M CaCl$_2$
10 ml 1% sodium citrate (m/v)
0.01 ml 1M MgSO$_4$
59.990 ml distilled water Example 6

Preparation of Competent Cells from *Bacillus subtilis*

A single colony of *Bacillus subtilis* is grown overnight in 5 ml of HS medium at 37° C. The next day, 500 µl of this culture is incubated with 50 ml of HS medium and again grown under vigorous stirring at 200 rpm. When the cells have reached the steady state, 10 ml aliquots are collected every 15 minutes. 1 ml of glycerol is added to each aliquot, which is left on ice for 15 minutes. 1 ml aliquots are then taken and stored at −80° C. until use. The fractions with the highest rate of transformation are used for the following transformations.

Example 7

Transformation of Competent *Bacillus subtilis* Cells and their Selection on IPTG Gradient The bacterial cells rendered competent are thawed rapidly in a thermostatic bath at 37° C., diluted in 20 ml of LS medium in a 250 ml Erlenmeyer flask, and placed under stirring for 2 hours at 30° C. When that time has elapsed, 1 ml aliquots are placed in 15 ml tubes to which 10 µl of EDTA is added, and maintained at ambient temperature for 5 minutes. Plasmid DNA pBS5 is added to the test tube and incubated for 2 h at 37° C., under stirring, with the maximum aeration. After gentle centrifugation the cells are plated in pre-heated selective medium. The bacterial colonies are obtained after two days. The cells cannot be grown in solution because they grow very slowly, and die after the addition of IPTG; above all, the few living cells no longer contain the recombinant plasmid. To select viable bacteria able to express high levels of hyaluronic acid, the cells were plated in the presence of an IPTG gradient. As shown in FIG. 6, the cells placed near a high concentration of IPTG die (because the tuaD expressed at high levels is toxic to *B. subtilis*); however, the cells plated in a position where a lower dose of IPTG occurs survived.

When the latter were examined, they presented as large, translucent colonies (FIG. 7), indicating the expression of hyaluronic acid; these cells, selected and grown in the presence of IPTG, also survive at higher doses of IPTG and preserve the plasmid during fermentation.

Through this system of selection viable bacterial lines are obtained, which are stable and above all secrete high levels of hyaluronic acid even after many cell divisions.

The stability of the plasmid was verified by growing the cells for 24 hours in the presence of IPTG and saccharose, and in the presence or absence of chloramphenicol. As clearly shown in FIG. 8, the number of colonies remains identical, demonstrating what has been stated, because plasmid contains chloramphenicol resistance gene, while the strain which has not been transfected, is devoid of said gene.

Example 8

Fermentation of Transformed, Selected *B. subtilis* Cells

*Bacillus subtilis* cells transformed with pBS5 plasmid and selected on IPTG gradient were cultured in a 20 L fermenter in 5 L of MM++ medium and glucose or saccharose as carbon source.

IPTG was added as inductor after the start of fermentation.

In the following, some fermentation processes for the production of HA having different weight average molecular weights are illustrated, said processes mainly differing because of:
  the starting source of carbon;
  the added feed (glucose or saccharose), activated about 7 hours after induction with IPTG 0.4-0.5 mM;
  the occurred fermentation time and therefore the final cells mass obtained;
  the temperature of fermentation (the temperature of fermentation can be established in a range between 20° C. and 38° C.).

Example 8A

Production of HA Having a Weight Average MW Comprised in the Range of 100-500 KD The bacterial strain *B. Subtilis* 1012, transfected with the plasmid pBS5 selected in IPTG gradient as described in Example 7, was used.

Procedure: a single colony resistant to IPTG was inoculated into 5 ml of sterile LB medium containing 10 µM of chloramphenicol, 10 µM of neomycin and 0.05 mM of IPTG. The culture was grown at 37° C., under stirring at 200 rpm.

After 8 hours, 50 µl of this culture were inoculated into a flask containing 50 ml of the medium mentioned above (with 0.5 mM of IPTG), and it was made to grow under the same conditions described above.

Subsequently, spent further 14-16 hours, 2 ml of this culture were inoculated into a flask containing 500 ml of the medium above, and it was made to grow under the same conditions until reaching a O.D.$^{600nm}$ of 0.6-0.8.

500 ml of the culture thus obtained were then inoculated in the fermenter and the fermentation conditions involved maintaining the culture under stirring at 1300 rpm, aeration with 10-12 liters of air/min, a temperature of 37° C. and a pH of 6.9 to 7.1. The initial source of carbon was 1% glucose.

After 6 hours of fermentation, a 2% glucose supply was added. At 24 hours of fermentation, IPTG was added to a final concentration of 0.4 mM; this induction proceeded for 6 hours; at the end, 10% glucose was added in stages.

At the end of fermentation (130 hours), the bacterial culture was discharged and centrifuged at 7500 rpm at 8° C. for 20 minutes.

The fermentation broth thus obtained, clarified as free of the cellular component, was analyzed to determine the concentration of HA with the carbazole method (Bitter and Muir, 1962, *Anal. Biochem.* 4:330-334).

Results: The analysis resulted in a concentration of HA of 7.5 g/l.

Determination of weight average molecular weight MW:

For its analysis it was used the method of the intrinsic viscosity (as described in Terbojevich et al., *Carbohydr. Res.* 1986, 363-377, incorporated herein by reference).

Results: the analyzed HA sample showed a weight average molecular weight MW in the range of 200-400 KD.

Culture media used:

LB broth (Miller), pH 7

MM++ (Minimal Medium Bs), containing per liter:

5 g $NH_4Cl$; 1 g $NH_4NO_3$; 3 g $K_2HPO_4$; 1 g $KH_2PO_4$; 1 g $Na_2SO_4$ to the sterile media they were added 100 ml of a sterile solution containing:

0.1 g $MgSO_4 \cdot 7H_2O$; 0.005 g $CaCl_2 \cdot 2H_2O$; 2 ml biotine solution (biotine solution 1 mg/l); 1 ml Fe solution ($FeCl_3$ solution 0.2M); yeast extract 5 g/l, 0.01% Hydrolyzed Casein; uracil 5 mg/l, DL-tryptophan 5 mg/l; Histidine 400 µg/l; Arginine 400 µg/l; glucose solution (1% per liter).

Example 8B

Production of HA Having a Weight Average MW Comprised in the Range of 500-1000 KD The bacterial strain *B. Subtilis* WB800N, transfected with the plasmid pBS5 selected in IPTG gradient as described in Example 7, was used.

Procedure: a single colony resistant to IPTG was treated as above disclosed according to example 8a. The initial source of carbon was saccharose at 2%. The fermentation conditions involved maintaining the culture under stirring at 600 rpm, aeration with 22-24 liters of air/min, a temperature of 37° C. and a pH of 6.9 to 7.1.

After 6 hours of fermentation, IPTG was added to a final concentration of 0.4 mM; this induction proceeded for about 4 hours; at the end, 3% saccharose was added in stages, monitoring its concentration in the culture up to the end of fermentation (ended after 62 hours).

The culture media used for the fermentation were those disclosed according to example 8a.

At the end of the process, the fermentation broth was analyzed to determine the concentration of HA with the carbazole method.

Results: the analysis resulted in a concentration of HA of 4.0 g/l.

Determination of weight average molecular weight MW:

For its analysis it was used the method of the intrinsic viscosity as indicated in the previous example 8a.

Results: the analyzed HA sample showed a weight average molecular weight MW in the range of 550-800 KD.

Example 8C

Production of HA Having a Weight Average MW Comprised in the Range of $1 \times 10^6$-$2 \times 10^6$ D The bacterial strain *B. Subtilis* 1012, transfected with the plasmid pBS5 selected in IPTG gradient as described in Example 7, was used.

Procedure: a single colony resistant to IPTG was treated as above disclosed according to example 8a. The initial source of carbon was saccharose at 2%: in this example the further supply was glucose (further experimental tests showed that it can be substituted with equal or lower amounts of saccharose). The fermentation conditions were the same as those used in example 8a, but the fermentation temperature was of 30° C.

The culture media used for the fermentation were those disclosed according to example 8a.

Cell mass development was of 30 g/l after 20 hours.

At the end of the process (ended after 35 hours), the fermentation broth was analyzed to determine the concentration of HA with the carbazole method.

Results: the analysis resulted in a concentration of HA of 3.3 g/l.

Determination of weight average molecular weight MW:

For its analysis it was used the method of the intrinsic viscosity as indicated in the previous example 8a.

Results: the analyzed HA sample showed a weight average molecular weight MW in the range of $1.5 \times 10^6$-$2 \times 10^6$ D.

The system engineered in *B. subtilis* is inducible, so the fermentation process can be continued by stimulating the production of HA to obtain the desired weight average molecular weight MW; fermentation times between 80 and 160 hours result in a medium-low weight average molecular weight MW, comprised in the range between 100-500 KD, fermentation times between 40 and 80 hours result in a weight average molecular weight in the range between 500-1000 KD, fermentation times between 12 and 40 hours result in a weight average molecular weight MW in the range $1 \times 10^6$-$2 \times 10^6$ D. With the experiments and the results obtained above, the Applicant has demonstrated to have perfected a system of production of HA in *B. subtilis* by plasmid vectors by:

- engineering of 2 genes (or 4 genes) plasmid vectors for the synthesis of enzymes needed for the production of said polysaccharide, whose gene control is placed under the control of inducible promoter Pgrac;
- perfecting a system of selection of these transfected strains of *B. subtilis*, for the production of stable, viable, replicating and HA secreting strains;
- creating an inducible system of HA production, thus controllable both in order to obtain high concentrations of HA and for the production of said polysaccharide at different weight average molecular weight MW.

The invention claimed is:

1. A process for the production of hyaluronic acid in *Bacillus subtilis*, wherein said process comprises:
   (a) culturing *Bacillus subtilis* cells transformed with a grac-lac system, in a medium under conditions suitable for producing hyaluronic acid, and in the presence of isopropyl-β-thiogalactopyranoside (IPTG) as an inducer, wherein said *Bacillus subtilis* cells are transformed with:
      (i) at least one episomal plasmid vector comprising a sequence coding for a hyaluronan synthase, and a sequence coding for a UDP-glucose dehydrogenase in tandem, under the control of a single strong inducible promoter Pgrac which uses the lac repressor, or
      (ii) at least one episomal plasmid vector comprising a sequence coding for a hyaluronan synthase, a sequence coding for a UDP-glucose dehydrogenase, a sequence coding for a UDP-glucose pyrophosphorylase and a sequence coding for a glucose 6 phosphate isomerase, under the control of a single strong inducible promoter Pgrac which uses the lac repressor; and
   (b) recovering hyaluronic acid from the culture medium; wherein said *Bacillus subtilis* cells transformed with the plasmid vector of (i) or (ii) are preselected on an IPTG gradient; and
   wherein hyaluronic acid having a weight average molecular weight in the range 100-500 KD is produced when the fermentation time is 80-160 hours; hyaluronic acid having a weight average molecular weight in the range 500-1000 KD is produced when the fermentation time is 40-80 hours; or hyaluronic acid having a weight average molecular weight in the range $1 \times 10^6$-$2 \times 10^6$ D is produced when the fermentation time is 12-40 hours.

2. The process according to claim 1, wherein the episomal plasmid vector (i) or (ii) further comprises a sequence coding for the lac repressor.

3. The process according to claim 1, wherein the IPTG inducer is added in step a) in quantities of between 0.01 and 10 mM in solution.

4. The process according to claim 1, wherein said *Bacillus subtilis* cells are *B. subtilis* WB800N or *B. subtilis* 1012 cells.

5. The process according to claim 1, wherein the hyaluronan synthase (hasA) is obtained from a strain of *Streptococcus* and the UDP-glucose dehydrogenase (hasB or tuaD), UDP-glucose pyrophosphorylase (hasC or gtaB) and glucose 6 phosphate isomerase (hasE or pgi) are obtained from *Bacillus subtilis*.

6. The process according to claim 1, wherein the sequences coding for the hyaluronan synthase, UDP-glucose dehydrogenase, UDP-glucose pyrophosphorylase and glucose 6 phosphate isomerase comprise an upstream Shine-Dalgarno sequence.

7. The process according to claim 1, wherein said plasmid vector of (i) comprises SEQ ID NO:1.

8. The process according to claim 1, wherein hyaluronic acid having a weight average molecular weight in the range 100-500 KD is produced when the fermentation time is 80-160 hours.

9. The process according to claim 1, wherein hyaluronic acid having a weight average molecular weight comprised in the range 500-1000 KD is produced when the fermentation time is 40-80 hours.

10. The process according to claim 1, wherein hyaluronic acid having a weight average molecular weight comprised in the range $1 \times 10^6$-$2 \times 10^6$ D is produced when the fermentation time is 12-40 hours.

11. The process according to claim 3, wherein the IPTG inducer is added in step (a) in quantities of between 0.01 and 5 mM or between 0.4 mM and 1 mM in solution.

12. The process according to claim 5, wherein the hyaluronan synthase (hasA) is obtained from a strain of *Streptococcus zooepidemicus*.

* * * * *

SEQUENCE LISTING

```
<160> NUMBER OF SEQ ID NOS: 12

<210> SEQ ID NO 1
<211> LENGTH: 10632
<212> TYPE: DNA
<213> ORGANISM: Artificial Sequence
<220> FEATURE:
<223> OTHER INFORMATION: Plasmid containing hasA and tuaD gene under the
      control of promoter grac
```

<400> SEQUENCE: 1

```
ttaagttatt ggtatgactg gttttaagcg caaaaaaagt tgcttttcg tacctattaa      60
tgtatcgttt tagaaaaccg actgtaaaaa gtacagtcgg cattatctca tattataaaa     120
gccagtcatt aggcctatct gacaattcct gaatagagtt cataaacaat cctgcatgat    180
aaccatcaca aacagaatga tgtacctgta aagatagcgg taaatatatt gaattacctt    240
tattaatgaa ttttcctgct gtaataatgg gtagaaggta attactatta ttattgatat    300
ttaagttaaa cccagtaaat gaagtccatg gaataataga aagagaaaaa gcattttcag    360
gtataggtgt tttgggaaac aatttccccg aaccattata tttctctaca tcagaaaggt    420
ataaatcata aaactctttg aagtcattct ttacaggagt ccaaatacca gagaatgttt    480
tagatacacc atcaaaaatt gtataaagtg gctctaactt atcccaataa cctaactctc    540
cgtcgctatt gtaaccagtt ctaaaagctg tatttgagtt tatcacccctt gtcactaaga   600
aaataaatgc agggtaaaat ttatatcctt cttgttttat gtttcggtat aaaacactaa    660
tatcaatttc tgtggttata ctaaaagtcg tttgttggtt caaataatga ttaaatatct    720
cttttctctt ccaattgtct aaatcaattt tattaaagtt catttgatat gcctcctaaa    780
tttttatcta aagtgaattt aggaggctta cttgtctgct ttcttcatta gaatcaatcc    840
tttttttaaaa gtcaatatta ctgtaacata aatatatatt ttaaaaatat cccactttat   900
ccaatttcg tttgttgaac taatgggtgc tttagttgaa gaataaagac cacattaaaa     960
aatgtggtct tttgtgtttt tttaaaggat ttgagcgtag cgaaaaatcc ttttctttct   1020
tatcttgata ataagggtaa ctattgccga tcgtccattc cgacagcatc gccagtcact   1080
atggcgtgct gctagcgcca ttcgccattc aggctgcgca actgttggga agggcgatcg   1140
gtgcgggcct cttcgctatt acgccagctg gcgaaagggg gatgtgctgc aaggcgatta   1200
agttgggtaa cgccagggtt ttcccagtca cgacgttgta aaacgacggc cagtgaattc   1260
gagctcaggc cttaactcac attaattgcg ttgcgctcac tgcccgcttt ccagtcggga   1320
aacctgtcgt gccagctgca ttaatgaatc ggccaacgcg cggggagagg cggtttgcgt   1380
attgggcgcc agggtggttt tcttttcac cagtgagacg gcaacagct gattgccctt     1440
caccgcctgg ccctgagaga gttgcagcaa gcggtccacg ctggtttgcc ccagcaggcg   1500
aaaatcctgt ttgatggtgg ttgacggcgg gatataacat gagctgtctt cggtatcgtc   1560
gtatcccact accgagatat ccgcaccaac gcgcagcccg gactcggtaa tggcgcgcat   1620
tgcgcccagc gccatctgat cgttggcaac cagcatcgca gtgggaacga tgccctcatt   1680
cagcatttgc atggtttgtt gaaaaccgga catggcactc cagtcgcctt cccgttccgc   1740
tatcggctga atttgattgc gagtgagata tttatgccag ccagccagac gcagacgcgc   1800
cgagacagaa cttaatgggc ccgctaacag cgcgatttgc tggtgaccca atgcgaccag   1860
atgctccacg cccagtcgcg taccgtcttc atgggagaaa ataatactgt tgatgggtgt   1920
ctggtcagag acatcaagaa ataacgccgg aacattagtg caggcagctt ccacagcaat   1980
ggcatcctgg tcatccagcg gatagttaat gatcagccca ctgacgcgtt gcgcgagaag   2040
attgtgcacc gccgctttac aggcttcgac gccgcttcgt tctaccatcg acaccaccac   2100
gctggcaccc agttgatcgg cgcgagattt aatcgccgcg acaatttgcg acggcgcgtg   2160
cagggccaga ctgaggtgg caacgccaat cagcaacgac tgtttgcccg ccagttgttg    2220
tgccacgcgg ttgggaatgt aattcagctc cgccatcgcc gcttccactt tttcccgcgt   2280
```

```
tttcgcagaa acgtggctgg cctggttcac cacgcgggaa acggtctgat aagagacacc    2340
ggcatactct gcgacatcgt ataacgttac tggtttcatc aaaatcgtct ccctccgttt    2400
gaatatttga ttgatcgtaa ccagatgaag cactctttcc actatcccta cagtgttatg    2460
gcttgaacaa tcacgaaaca ataattggta cgtacgatct ttcagccgac tcaaacatca    2520
aatcttacaa atgtagtctt tgaaagtatt acatatgtaa gatttaaatg caaccgtttt    2580
ttcggaagga aatgatgacc tcgtttccac cggaattagc ttggtaccag ctattgtaac    2640
ataatcggta cggggggtgaa aaagctaacg gaaaagggag cggaaaagaa tgatgtaagc    2700
gtgaaaaatt ttttatctta tcacttgaaa ttggaaggga gattcttat tataagaatt      2760 gtggaattgt gagcggataa caattcccaa ttaaggagg aaggatccat gagaacatta       2820
aaaaacctca taactgttgt ggcctttagt attttttggg tactgttgat ttacgtcaat    2880
gtttatctct ttggtgctaa aggaagcttg tcaatttatg gcttttttgct gatagcttac   2940 ctattagtca aaatgtcctt atccttttt tacaagccat ttaagggaag gctgggcaa       3000 tataaggttg cagccattat tccctcttat aacgaagatg ctgagtcatt gctagagacc    3060
ttaaaaagtg ttcagcagca aacctatccc ctagcagaaa tttatgttgt tgacgatgga    3120
agtgctgatg agacaggtat taagcgcatt gaagactatg tgcgtgacac tggtgaccta    3180
tcaagcaatg tcattgttca ccggtcagaa aaaaatcaag gaaagcgtca tgcacaggcc    3240
tgggcctttg aaagatcaga cgctgatgtc ttttttgaccg ttgactcaga tacttatatc   3300
taccctgatg ctttagagga gttgttaaaa acctttaatg acccaactgt ttttgctgcg    3360
acgggtcacc ttaatgtcag aaatagacaa accaatctct taacacgctt gacagatatt    3420
cgctatgata atgcttttgg cgttgaacga gctgcccaat ccgttacagg taatattctc    3480
gtttgctcag gcccgcttag cgtttacaga cgcgaggtgg ttgttcctaa catagataga    3540
tacatcaacc agaccttcct gggtattcct gtaagtatcg gtgatgacag gtgcttgacc    3600
aactatgcaa ctgatttagg aaagactgtt tatcaatcca ctgctaaatg tattacagat    3660
gttcctgaca agatgtctac ttacttgaag cagcaaaacc gctggaacaa gtccttcttt    3720
agagagtcca ttatttctgt taagaaaatc atgaacaatc cttttgtagc cctatggacc    3780
atacttgagg tgtctatgtt tatgatgctt gtttattctg tggtggattt cttttgtaggc   3840 aatgtcagag aatttgattg gctcagggtt ttggcctttc tggtgattat cttcattgtt    3900
gctctttgtc gtaatattca ctatatgctt aagcacccgc tgtccttctt gttatctccg    3960
ttttatgggg tactgcattt gtttgtccta cagcccttga aattgtattc tcttttttact   4020 attagaaatg ctgactgggg aacacgtaaa aaattattat aatctagaaa taattttgtt    4080
taactttaag aaggagatat acatatgaaa aaaatagctg tcattggaac aggttatgta    4140
ggactcgtat caggcacttg ctttgcggag atcggcaata agttgtttg ctgtgatatc     4200 gatgaatcaa aaatcagaag cctgaaaaat ggggtaatcc caatctatga accagggctt    4260
gcagacttag ttgaaaaaaa tgtgctggat cagcgcctga cctttacgaa cgatatcccg    4320
tctgccattc gggcctcaga tattatttat attgcagtcg gaacgcctat gtccaaaaca    4380
ggtgaagctg atttaacgta cgtcaaagcg gcggcgaaaa caatcggtga gcatcttaac    4440
ggctacaaag tgatcgtaaa taaaagcaca gtcccggttg aacagggaa actggtgcaa    4500 tctatcgttc aaaagcctc aaaggggaga tactcatttg atgttgtatc taaccctgaa     4560
ttccttcggg aagggtcagc gattcatgac acgatgaata tggagcgtgc cgtgattggt    4620
tcaacaagtc ataaagccgc tgccatcatt gaggaacttc atcagccatt ccatgctcct    4680
```

```
gtcattaaaa caaacctaga aagtgcagaa atgattaaat acgccgcgaa tgcatttctg    4740
gcgacaaaga tttcctttat caacgatatc gcaaacattt gtgagcgagt cggcgcagac    4800
gtttcaaaag ttgctgatgg tgttggtctt gacagccgta tcggcagaaa gttccttaaa    4860
gctggtattg gattcggcgg ttcatgtttt ccaaaggata caaccgcgct gcttcaaatc    4920
gcaaaatcgg caggctatcc attcaagctc atcgaagctg tcattgaaac gaacgaaaag    4980
cagcgtgttc atattgtaga taaacttttg actgttatgg gaagcgtcaa agggagaacc    5040
atttcagtcc tgggattagc cttcaaaccg aatacgaacg atgtgagatc cgctccagcg    5100
cttgatatta tcccaatgct gcagcagctg gcgcgcccatg taaaagcata cgatccgatt    5160
gctattcctg aagcttcagc gatccttggc gaacaggtcg agtattacac agatgtgtat    5220
gctgcgatga agacactga tgcatgcctg atttttaacgg attggccgga agtgaaagaa    5280
atggagcttg taaaagtgaa aaccctctta aaacagccag tcatcattga cggcagaaat    5340
ttattttcac ttgaagagat gcaggcagcc ggatacattt atcactctat cggccgtccc    5400
gctgttcggg gaacggaacc ctctgacaag tattttccgg gcttgccgct gaagaattg    5460 gctaaagact tgggaagcgt caatttataa gctagagtcg acgtccccgg ggcagcccgc    5520
ctaatgagcg ggcttttttc acgtcacgcg tccatggaga tctttgtctg caactgaaaa    5580
gtttatacct tacctggaac aaatggttga aacatacgag gctaatatcg gcttattagg    5640
aatagtccct gtactaataa aatcaggtgg atcagttgat cagtatattt tggacgaagc    5700
tcggaaagaa tttggagatg acttgcttaa ttccacaatt aaattaaggg aaagaataaa    5760
gcgatttgat gttcaaggaa tcacggaaga agatactcat gataaagaag ctctaaaact    5820
attcaataac cttacaatgg aattgatcga aagggtggaa ggttaatggt acgaaaatta    5880
ggggatctac ctagaaagcc acaaggcgat aggtcaagct taaagaaccc ttacatggat    5940
cttacagatt ctgaaagtaa agaaacaaca gaggttaaac aaacagaacc aaaaagaaaa    6000
aaagcattgt tgaaaacaat gaaagttgat gtttcaatcc ataataagat taaatcgctg    6060
cacgaaattc tggcagcatc cgaagggaat tcatattact tagaggatac tattgagaga    6120
gctattgata agatggttga gacattacct gagagccaaa aaacttttta tgaatatgaa    6180
ttaaaaaaaa gaaccaacaa aggctgagac agactccaaa cgagtctgtt tttttaaaaa    6240
aaatattagg agcattgaat atatattaga gaattaagaa agacatggga ataaaaatat    6300
tttaaatcca gtaaaaatat gataagatta tttcagaata tgaagaactc tgtttgtttt    6360
tgatgaaaaa acaaacaaaa aaaatccacc taacggaatc tcaatttaac taacagcggc    6420
caaactgaga agttaaattt gagaagggga aaggcggat ttatacttgt atttaactat    6480
ctccatttta acatttttatt aaaccccata caagtgaaaa tcctctttta cactgttcct    6540
ttaggtgatc gcggagggac attatgagtg aagtaaacct aaaaggaaat acagatgaat    6600
tagtgtatta tcgacagcaa accactggaa ataaaatcgc caggaagaga atcaaaaaag    6660
ggaaagaaga agtttattat gttgctgaaa cggaagagaa gatatggaca gaagagcaaa    6720
taaaaaactt ttcttagac aaatttggta cgcatatacc ttacatagaa ggtcattata    6780
caatcttaaa taattacttc tttgattttt ggggctattt tttaggtgct gaaggaattg    6840
cgctctatgc tcacctaact cgttatgcat acggcagcaa agacttttgc tttcctagtc    6900
tacaaacaat cgctaaaaaa atggacaaga ctcctgttac agttagaggc tacttgaaac    6960
tgcttgaaag gtacggtttt atttggaagg taaacgtccg taataaaacc aaggataaca    7020
```

```
cagaggaatc cccgattttt aagattagac gtaaggttcc tttgctttca gaagaacttt   7080
taaatggaaa ccctaatatt gaaattccag atgacgagga agcacatgta aagaaggctt   7140
taaaaaagga aaagagggt cttccaaagg ttttgaaaaa agagcacgat gaatttgtta    7200
aaaaaatgat ggatgagtca gaaacaatta atattccaga ggccttacaa tatgacacaa   7260
tgtatgaaga tatactcagt aaaggagaaa ttcgaaaaga aatcaaaaaa caaataccta   7320
atcctacaac atcttttgag agtatatcaa tgacaactga agaggaaaaa gtcgacagta   7380 cttttaaaaag cgaaatgcaa aatcgtgtct ctaagccttc ttttgatacc tggtttaaaa   7440
acactaagat caaaattgaa aataaaaatt gtttattact tgtaccgagt gaatttgcat   7500
ttgaatggat taagaaaaga tatttagaaa caattaaaac agtccttgaa gaagctggat   7560
atgttttcga aaaatcgaa ctaagaaaag tgcaataaac tgctgaagta tttcagcagt     7620
tttttttatt tagaaatagt gaaaaaaata taatcaggga ggtatcaata tttaatgagt   7680
actgatttaa atttatttag actggaatta ataattaaca cgtagactaa ttaaaattta   7740
atgagggata aagaggatac aaaaatatta atttcaatcc ctattaaatt ttaacaaggg   7800
ggggattaaa atttaattag aggtttatcc acaagaaaag accctaataa aatttttact   7860
agggttataa cactgattaa tttcttaatg ggggagggat taaaatttaa tgacaaagaa   7920
aacaatcttt taagaaaagc ttttaaaaga taataataaa aagagctttg cgattaagca   7980
aaactcttta cttttcatt gacattatca aattcatcga tttcaaattg ttgttgtatc    8040
ataaagttaa ttctgttttg cacaaccttt tcaggaatat aaaacacatc tgaggcttgt   8100
tttataaact cagggtcgct aaagtcaatg taacgtagca tatgatatgg tatagcttcc   8160
acccaagtta gccttctgc ttcttctgaa tgttttcat atacttccat gggtatctct      8220
aaatgatttt cctcatgtag caaggtatga gcaaaaagtt tatggaattg atagttcctc   8280
tcttttcttt caactttttt atctaaaaca aacactttaa catctgagtc aatgtaagca   8340
taagatgttt ttccagtcat aatttcaatc ccaaatcttt tagacagaaa ttctggacgt   8400
aaatcttttg gtgaaagaat tttttatgt agcaatatat ccgatacagc accttctaaa    8460
agcgttggtg aatagggcat tttacctatc tcctctcatt ttgtggaata aaaatagtca   8520
tattcgtcca tctacctatc ctattatcga acagttgaac ttttttaatca aggatcagtc   8580 cttttttca ttattcttaa actgtgctct taactttaac aactcgatt gttttttccag     8640 atctcgaggg taactagcct cgccgatccc gcaagaggcc cggcagtcag gtggcacttt   8700
tcggggaaat gtgcgcggaa cccctatttg tttattttc taaatacatt caaatatgta    8760
tccgctcatg agacaataac cctgataaat gcttcaataa tattgaaaaa ggaagagtat   8820
gagtattcaa catttccgtg tcgcccttat tcccttttttt gcggcatttt gccttcctgt   8880
ttttgctcac ccagaaacgc tggtgaaagt aaaagatgct gaagatcagt tgggtgcacg   8940
agtgggttac atcgaactgg atctcaacag cggtaagatc cttgagagtt ttcgccccga   9000
agaacgtttt ccaatgatga gcacttttaa agttctgcta tgtggcgcgg tattatcccg   9060
tattgacgcc gggcaagagc aactcggtcg ccgcatacac tattctcaga atgacttggt   9120
tgagtactca ccagtcacag aaaagcatct tacggatggc atgacagtaa gagaattatg   9180
cagtgctgcc ataaccatga gtgataacac tgcggccaac ttacttctga caacgatcgg   9240
aggaccgaag gagctaaccg cttttttgca acatggggg atcatgtaa ctcgccttga    9300 tcgttgggaa ccggagctga atgaagccat accaaacgac gagcgtgaca ccacgatgcc   9360
tgtagcaatg gcaacaacgt tgcgcaaact attaactggc gaactactta ctctagcttc   9420
```

```
ccggcaacaa ttaatagact ggatggaggc ggataaagtt gcaggaccac ttctgcgctc    9480
ggcccttccg gctggctggt ttattgctga taaatctgga gccggtgagc gtgggtctcg    9540
cggtatcatt gcagcactgg ggccagatgg taagccctcc cgtatcgtag ttatctacac    9600
gacggggagt caggcaacta tggatgaacg aaatagacag atcgctgaga taggtgcctc    9660
actgattaag cattggtaac tgtcagacca agtttactca tatatacttt agattgattt    9720
aaaacttcat ttttaattta aaaggatcta ggtgaagatc cttttttgata atctcatgac   9780 caaaatccct taacgtgagt tttcgttcca ctgagcgtca gaccccgtag aaaagatcaa    9840
aggatcttct tgagatcctt ttttttctgcg cgtaatctgc tgcttgcaaa caaaaaaacc    9900
accgctacca gcggtggttt gtttgccgga tcaagagcta ccaactcttt ttccgaaggt    9960
aactggcttc agcagagcgc agataccaaa tactgtcctt ctagtgtagc cgtagttagg   10020
ccaccacttc aagaactctg tagcaccgcc tacatacctc gctctgctaa tcctgttacc   10080
agtggctgct gccagtggcg ataagtcgtg tcttaccggg ttggactcaa gacgatagtt   10140
accggataag gcgcagcggt cgggctgaac ggggggttcg tgcacacagc ccagcttgga   10200
gcgaacgacc tacaccgaac tgagatacct acagcgtgag ctatgagaaa gcgccacgct   10260
tcccgaaggg agaaaggcgg acaggtatcc ggtaagcggc agggtcggaa caggagagcg   10320
cacgagggag cttccagggg gaaacgcctg gtatctttat agtcctgtcg ggtttcgcca   10380
cctctgactt gagcgtcgat ttttgtgatg ctcgtcaggg gggcggagcc tatggaaaaa   10440
cgccagcaac gcggcctttt tacggttcct ggccttttgc tggccttttg ctcacatgtt   10500
ctttcctgcg ttatcccctg attctgtgga taaccgtatt accgcctttg agtgagctga   10560
taccgctcgc cgcagccgaa cgaccgagcg cagcgagtca gtgagcgagg aagcggaaga   10620
gcgcccaata cg                                                       10632

<210> SEQ ID NO 2
<211> LENGTH: 27
<212> TYPE: DNA
<213> ORGANISM: Artificial Sequence
<220> FEATURE:
<223> OTHER INFORMATION: tuaD gene amplification primer

<400> SEQUENCE: 2
atgaaaaaat agctgtcatt ggaacag                                         27

<210> SEQ ID NO 3
<211> LENGTH: 24
<212> TYPE: DNA
<213> ORGANISM: Artificial Sequence
<220> FEATURE:
<223> OTHER INFORMATION: tuaD gene amplification primer

<400> SEQUENCE: 3
ttataaattg tcgttcccaa gtct                                            24

<210> SEQ ID NO 4
<211> LENGTH: 31
<212> TYPE: DNA
<213> ORGANISM: Artificial Sequence
<220> FEATURE:
<223> OTHER INFORMATION: tuaD gene cloning primer

<400> SEQUENCE: 4
gctggatcca tgaaaaaata gctgtcattg g                                    31
```

<210> SEQ ID NO 5
<211> LENGTH: 31
<212> TYPE: DNA
<213> ORGANISM: Artificial Sequence
<220> FEATURE:
<223> OTHER INFORMATION: tuaD gene cloning primer

<400> SEQUENCE: 5
ctcgctagct tataaattga cgcttcccaa g                                    31

<210> SEQ ID NO 6
<211> LENGTH: 28
<212> TYPE: DNA
<213> ORGANISM: Artificial Sequence
<220> FEATURE:
<223> OTHER INFORMATION: Amplification primer for the introduction of a
      Shine-Dalgarno sequence in the tuaD gene

<400> SEQUENCE: 6
cgacatatga aaaatagct gtcattgg                                         28

<210> SEQ ID NO 7
<211> LENGTH: 31
<212> TYPE: DNA
<213> ORGANISM: Artificial Sequence
<220> FEATURE:
<223> OTHER INFORMATION: Amplification primer for the introduction of a
      Shine-Dalgarno sequence in the tuaD gene

<400> SEQUENCE: 7
ctcgctagct tataaattga cgcttcccaa g                                    31

<210> SEQ ID NO 8
<211> LENGTH: 26
<212> TYPE: DNA
<213> ORGANISM: Artificial Sequence
<220> FEATURE:
<223> OTHER INFORMATION: hasA gene amplification primer

<400> SEQUENCE: 8
atgagaacat taaaaaacct cataac                                          26

<210> SEQ ID NO 9
<211> LENGTH: 25
<212> TYPE: DNA
<213> ORGANISM: Artificial Sequence
<220> FEATURE:
<223> OTHER INFORMATION: hasA gene amplification primer

<400> SEQUENCE: 9
taataatttt ttacgtgttc cccag                                           25

<210> SEQ ID NO 10
<211> LENGTH: 32
<212> TYPE: DNA
<213> ORGANISM: Artificial Sequence
<220> FEATURE:
<223> OTHER INFORMATION: hasA gene cloning primer

<400> SEQUENCE: 10
ggaggatcca tgagaacatt aaaaaacctc at                                   32

<210> SEQ ID NO 11
<211> LENGTH: 31
<212> TYPE: DNA
<213> ORGANISM: Artificial Sequence

```
<220> FEATURE:
<223> OTHER INFORMATION: hasA gene cloning primer

<400> SEQUENCE: 11
cagtctagat tataataatt tttacgtgtc c                              31

<210> SEQ ID NO 12
<211> LENGTH: 153
<212> TYPE: DNA
<213> ORGANISM: Artificial Sequence
<220> FEATURE:
<223> OTHER INFORMATION: Synthetic oligonucleotide

<400> SEQUENCE: 12
gaaaagaatg atgtaagcgt gaaaaatttt ttatcttatc acttgaaatt ggaagggaga     60
ttctttatta taagaattgt ggaattgtga gcggataaca attcccaatt aaaggaggaa    120
ggatcctcta gagtcgacgt ccccggggca gcc                                153
```